US009416355B2

(12) United States Patent
Andersen et al.

(10) Patent No.: US 9,416,355 B2
(45) Date of Patent: Aug. 16, 2016

(54) ALPHA-AMYLASE VARIANTS AND POLYNUCLEOTIDES ENCODING SAME

(75) Inventors: Carsten Andersen, Vaerloese (DK); Randall Deinhammer, Wake Forest, NC (US); Thomas Agersten Poulsen, Ballerup (DK); Miguel Duarte Toscano, Copenhagen (DK); Peter Kamp Hansen, Lejre (DK); Henrik Friis-Madsen, Ballerup (DK); Anders Viksoe-Nielsen, Slangerup (DK); Signe Eskildsen Larsen, Lyngby (DK); Lars L. H. Christensen, Alleroed (DK)

(73) Assignees: NOVOZYMES NORTH AMERICA, INC., Franklinton, NC (US); NOVOZYMES A/S, Bagsvaerd (DK)

(*) Notice: Subject to any disclaimer, the term of this patent is extended or adjusted under 35 U.S.C. 154(b) by 555 days.

(21) Appl. No.: 13/515,437

(22) PCT Filed: Jan. 4, 2011

(86) PCT No.: PCT/US2011/020128
§ 371 (c)(1),
(2), (4) Date: Jun. 20, 2012

(87) PCT Pub. No.: WO2011/082425
PCT Pub. Date: Jul. 7, 2011

(65) Prior Publication Data
US 2012/0282658 A1    Nov. 8, 2012

Related U.S. Application Data

(60) Provisional application No. 61/292,324, filed on Jan. 5, 2010, provisional application No. 61/292,327, filed on Jan. 5, 2010, provisional application No. 61/304,092, filed on Feb. 12, 2010, provisional application No. 61/333,930, filed on May 12, 2010, provisional application No. 61/354,775, filed on Jun. 15, 2010, provisional application No. 61/354,817, filed on Jun. 15, 2010, provisional application No. 61/355,230, filed on Jun. 16, 2010, provisional application No. 61/362,536, filed on Jul. 8, 2010.

(30) Foreign Application Priority Data

Jan. 4, 2010 (EP) .................... 10150062
Jan. 4, 2010 (EP) .................... 10150063

(51) Int. Cl.
C12N 9/26     (2006.01)
C12N 9/28     (2006.01)
C12P 19/04    (2006.01)
C12P 7/06     (2006.01)
C12P 7/14     (2006.01)
C12P 19/14    (2006.01)
C11D 3/386    (2006.01)

(52) U.S. Cl.
CPC .............. *C12N 9/2417* (2013.01); *C11D 3/386* (2013.01); *C12N 9/2414* (2013.01); *C12P 7/06* (2013.01); *C12P 7/14* (2013.01); *C12P 19/04* (2013.01); *C12P 19/14* (2013.01); *C12Y 302/01001* (2013.01); *Y02E 50/17* (2013.01)

(58) Field of Classification Search
CPC ...................... C12N 9/2417; C12Y 302/01001; C08B 30/14; Y02E 50/07
See application file for complete search history.

(56) References Cited

U.S. PATENT DOCUMENTS

| | | | |
|---|---|---|---|
| 6,093,562 A * | 7/2000 | Bisg.ang.rd-Frantzen et al. | 435/202 |
| 6,297,038 B1 * | 10/2001 | Bisg.ang.rd-Frantzen et al. | 435/202 |
| 6,743,616 B2 | 6/2004 | Araki et al. | |
| 6,867,031 B2 * | 3/2005 | Bisgard-Frantzen et al. | 435/202 |
| 7,498,158 B2 * | 3/2009 | Svendsen et al. | 435/202 |
| 7,541,026 B2 * | 6/2009 | Power et al. | 424/94.6 |
| 8,084,240 B2 * | 12/2011 | Cuevas et al. | 435/202 |
| 8,512,986 B2 * | 8/2013 | Fukuyama | C12N 9/242 435/101 |
| 8,841,091 B2 * | 9/2014 | Fukuyama | C12N 9/2417 435/101 |
| 2002/0098996 A1 * | 7/2002 | Bisgard-Frantzen et al. | 510/392 |
| 2004/0096952 A1 * | 5/2004 | Svendsen et al. | 435/202 |
| 2006/0035323 A2 * | 2/2006 | Bisgard Frantzen et al. | 435/69.1 |
| 2006/0148054 A1 * | 7/2006 | Fukuyama | C12N 9/242 435/161 |
| 2009/0117642 A1 * | 5/2009 | Power et al. | 435/202 |
| 2009/0280527 A1 * | 11/2009 | Bisgard-Frantzen et al. | 435/69.1 |
| 2009/0314286 A1 * | 12/2009 | Cuevas et al. | 127/38 |
| 2010/0003366 A1 * | 1/2010 | Cuevas | C12N 9/2417 426/20 |
| 2010/0099597 A1 * | 4/2010 | Bisgard-Frantzen et al. | 510/226 |

(Continued)

FOREIGN PATENT DOCUMENTS

WO    95/10603 A1    4/1995
WO    96/23873 A1    8/1996

(Continued)

OTHER PUBLICATIONS

Ihara, H., et al., 1985, "Complete nucleotide sequence of a thermophilic alpha-amylase gene: homology between prokaryotic and eukaryotic alpha-amylases at the active sites", Journal of Biochemistry vol. 98, pp. 95-103.*

(Continued)

*Primary Examiner* — Manjunath Rao
*Assistant Examiner* — William W Moore
(74) *Attorney, Agent, or Firm* — Michael W. Krenicky

(57) ABSTRACT

The present invention relates to variants of a parent alpha-amylase. The present invention also relates to polynucleotides encoding the variants and to nucleic acid constructs, vectors, and host cells comprising the polynucleotides, and methods of using the variant enzymes.

16 Claims, 2 Drawing Sheets

(56) References Cited

U.S. PATENT DOCUMENTS

| | | | |
|---|---|---|---|
| 2011/0033882 A1* | 2/2011 | Aehle et al. | 435/22 |
| 2011/0104759 A1* | 5/2011 | Fukuyama | C12N 9/242 435/72 |
| 2011/0177990 A1* | 7/2011 | Bisgard-Frantzen et al. | 510/226 |
| 2012/0156733 A1* | 6/2012 | Cuevas et al. | 435/99 |
| 2012/0208251 A1* | 8/2012 | Svendsen et al. | 435/162 |
| 2014/0017749 A1* | 1/2014 | Deinhammer | C12Y 302/01001 435/161 |
| 2014/0127753 A1* | 5/2014 | Fukuyama | C12N 9/2417 435/99 |
| 2014/0370553 A1* | 12/2014 | Fukuyama | C12N 9/2417 435/99 |

FOREIGN PATENT DOCUMENTS

| | | |
|---|---|---|
| WO | 96/23874 A1 | 8/1996 |
| WO | 96/39528 A2 | 12/1996 |
| WO | 00/60059 A2 | 10/2000 |
| WO | 01/66712 A2 | 9/2001 |
| WO | 02/10355 A2 | 2/2002 |
| WO | 02/31124 A2 | 4/2002 |
| WO | 02/092797 A2 | 11/2002 |
| WO | 03/014358 A2 | 2/2003 |
| WO | 2006/069290 A2 | 6/2006 |
| WO | 2006/002643 A2 | 11/2006 |
| WO | 2009/061379 A2 | 5/2009 |

OTHER PUBLICATIONS

Gray, G. L., et al., 1986, "Structural genes encoding the thermophilic alpha-amylases of Bacillus stearothermophilus and Bacillus licheniformis", Journal of Bacteriology, vol. 166, No. 2, pp. 635-643.*

Ben Ali, M., et al., 2001, "Purification and sequence analysis of the atypical maltohexaose-forming alpha-amylaseof the B. stearothermophilus US100", Enzyme and Microbial Technology, vol. 28, pp. 537-542.*

Igarashi, K., et al., 1998, "Improved thermostability of a Bacillus alpha-amylase by deletion of an arginine-glycine residue is caused by enhanced calcium binding", Biochemical and Biophysical Research Communications, vol. 248, pp. 372-377.*

UniProtKB/TrEMBL database entry Q59222_9BACI, alpha-amylase (EC 3.2.2.1) of *Bacillus* sp. TS-23, integrated in 1996.*

Hatada et al., Enzyme and Microbial Technology, vol. 39, pp. 1333-1340 (2006).

Nielsen et al., Biochimica et Biophysics Acta, vol. 1543, pp. 253-274 (2000).

Priyadharshini et al., Biotechnology Letters, vol. 29, pp. 1493-1499 (2007).

* cited by examiner

```
                        1                                                 50
SEQ ID NO 1    (1)  --AAPFNGTMMQYFEWYLPDDGTLWTKVANEANNLSSLGITALWLPPAYK
SEQ ID NO 2    (1)  ---VPVNGTMMQYFEWYLPDDGTLWTKVANNAQSLANLGITALWLPPAYK
SEQ ID NO 3    (1)  -GSVPVNGTMMQYFEWYLPDDGTLWTKVANNAQSLANLGITALWLPPAYK
SEQ ID NO 4    (1)  ANTAPINETMMQYFEWDLPNDGTLWTKVKNEAANLSSLGITALWLPPAYK
SEQ ID NO 5    (1)  ---APVNGTMMQYFEWDLPNDGTLWTKVKNEASSLSSLGITALWLPPAYK
SEQ ID NO 7    (1)  --AAPFNGTMMQYFEWYLPDDGTLWTKVANEANNLSSLGITALWLPPAYK 51                                                100
SEQ ID NO 1   (49)  GTSRSDVGYGVYDLYDLGEFNQKGTVRTKYGTKAQYLQAIQAAHAAGMQV
SEQ ID NO 2   (48)  GTSSSDVGYGVYDLYDLGEFNQKGTVRTKYGTKTQYIQAIQAAHTAGMQV
SEQ ID NO 3   (50)  GTSSSDVGYGVYDLYDLGEFNQKGTVRTKYGTKTQYIQAIQAAHTAGMQV
SEQ ID NO 4   (51)  GTSQSDVGYGVYDLYDLGEFNQKGTIRTKYGTKTQYIQAIQAAKAAGMQV
SEQ ID NO 5   (48)  GTSQGDVGYGVYDLYDLGEFNQKGTIRTKYGTKTQYLQAIQAAKSAGMQV
SEQ ID NO 7   (49)  GTSRSDVGYGVYDLYDLGEFNQKGTVRTKYGTKAQYLQAIQAAHAAGMQV 101                                               150
SEQ ID NO 1   (99)  YADVVFDHKGGADGTEWVDAVEVNPSDRNQEISGTYQIQAWTKFDFPGRG
SEQ ID NO 2   (98)  YADVVFNHKAGADGTELVDAVEVNPSDRNQEISGTYQIQAWTKFDFPGRG
SEQ ID NO 3  (100)  YADVVFNHKAGADGTELVDAVEVNPSDRNQEISGTYQIQAWTKFDFPGRG
SEQ ID NO 4  (101)  YADVVFNHKAGADGTEFVDAVEVDPSNRNQETSGTYQIQAWTKFDFPGRG
SEQ ID NO 5   (98)  YADVVFNHKAGADSTEWVDAVEVNPSNRNQETSGTYQIQAWTKFDFPGRG
SEQ ID NO 7   (99)  YADVVFDHKGGADGTEWVDAVEVNPSDRNQEISGTYQIQAWTKFDFPGRG 151                                               200
SEQ ID NO 1  (149)  NTYSSFKWRWYHFDGVDWDESRKLSRIYKFRGIGKAWDWEVDTENGNYDY
SEQ ID NO 2  (148)  NTYSSFKWRWYHFDGTDWDESRKLNRIYKFRGTGKAWDWEVDTENGNYDY
SEQ ID NO 3  (150)  NTYSSFKWRWYHFDGTDWDESRKLNRIYKFRGTGKAWDWEVDTENGNYDY
SEQ ID NO 4  (151)  NTYSSFKWRWYHFDGTDWDESRKLNRIYKFRSTGKAWDWEVDTENGNYDY
SEQ ID NO 5  (148)  NTYSSFKWRWYHFDGTDWDESRKLNRIYKFRGTGKAWDWEVDTENGNYDY
SEQ ID NO 7  (149)  NTYSSFKWRWYHFDGVDWDESRKLSRIYKFRGIGKAWDWEVDTENGNYDY 201                                               250
SEQ ID NO 1  (199)  LMYADLDMDHPEVVTELKNWGKWYVNTTNIDGFRLDAVKHIKFSFFPDWL
SEQ ID NO 2  (198)  LMYADLDMDHPEVVSELKNWGKWYVTTTNIDGFRLDAVKHIKYSFFPDWL
SEQ ID NO 3  (200)  LMYADLDMDHPEVVSELKNWGKWYVITTNIDGFRLDAVKHIKYSFFPDWL
SEQ ID NO 4  (201)  LMFADLDMDHPEVVTELKNWGTWYVNTTNIDGFRLDAVKHIKYSFFPDWL
SEQ ID NO 5  (198)  LMFADLDMDHPEVVTELKNWGTWYVNTTNVDGFRLDAVKHIKYSFFPDWL
SEQ ID NO 7  (199)  LMYADLDMDHPEVVTELKNWGKWYVNTTNIDGFRLDAVKHIKFQFFPDWL 251                                               300
SEQ ID NO 1  (249)  SYVRSQTGKPLFTVGEYWSYDINKLHNYITKTNGTMSLFDAPLHNKFYTA
SEQ ID NO 2  (248)  SYVRTQTQKPLFAVGEFWSYDISKLHNYITKTNGSMSLFDAPLHNNFYIA
SEQ ID NO 3  (250)  SYLRTQTQKPLFAVGEFWSYDISKLHNYITKTNGSMSLFDAPLHNNFYIA
SEQ ID NO 4  (251)  TYVRNQTGKNLFAVGEFWSYDVNKLHNYITKTNGSMSLFDAPLHNNFYTA
SEQ ID NO 5  (248)  THVRSQTRKNLFAVGEFWSYDVNKLHNYITKTSGTMSLFDAPLHNNFYTA
SEQ ID NO 7  (249)  SYVRSQTGKPLFTVGEYWSYDINKLHNYITKTNGTMSLFDAPLHNKFYTA 301                                               350
SEQ ID NO 1  (299)  SKSGGAFDMRTLMTNTLMKDQPTLAVTFVDNHDTEPGQALQSWVDPWFKP
SEQ ID NO 2  (298)  SKSGGYFDMRTLLNNTLMKDQPTLAVTLVDNHDTEPGQSLQSWVEPWFKP
SEQ ID NO 3  (300)  SKSGGYFDMRTLLNNTLMKEQPTLSVTLVDNHDTEPGQSLQSWVEPWFKP
SEQ ID NO 4  (301)  SKSGGYFDMRYLLNNTLMKDQPSLAVTLVDNHDTQPGQSLQSWVEPWFKP
SEQ ID NO 5  (298)  SKSGGYFDMRYLLNNTLMKDQPSLAVTLVDNHDTQPGQSLQSWVEPWFKP
SEQ ID NO 7  (299)  SKSGGAFDMRTLMTNTLMKDQPTLAVTFVDNHDTEPGQALQSWVDPWFKP 351                                               400
SEQ ID NO 1  (349)  LAYAFILTRQEGYPCVFYGDYYGIPQYNIPSLKSKIDPLLIARRDYAYGT
SEQ ID NO 2  (348)  LAYAFILTRQEGYPCVFYGDYYGIPKYNIPALKSKLDPLLIARRDYAYGT
SEQ ID NO 3  (350)  LAYAFILTRQEGYPCVFYGDYYGIPKYNIPALKSKLDPLLIARRDYAYGT
SEQ ID NO 4  (351)  LAYAFILTRQEGYPCVFYGDYYGIPKYNIPGLKSKIDPLLIARRDYAYGT
SEQ ID NO 5  (348)  LAYAFILTRQEGYPCVFYGDYYGIPKYNIPGLKSKIDPLLIARRDYAYGT
SEQ ID NO 7  (349)  LAYAFILTRQEGYPCVFYGDYYGIPQYNIPSLKSKIDPLLIARRDYAYGT
```

Fig. 1(a)

```
              401                                             450
SEQ ID NO 1  (399) QHDYLDHSDIIGWTREGVTEKPGSGLAALITDGPGGSKWMYVGKQHAGKV
SEQ ID NO 2  (398) QHDYIDSADIIGWTREGVAEKANSGLAALITDGPGGSKWMYVGKQHAGKT
SEQ ID NO 3  (400) QHDYIDNADIIGWTREGVAEKANSGLAALITDGPGGSKWMYVGKQHAGKT
SEQ ID NO 4  (401) QRDYIDHQDIIGWTREGIDTKPNSGLAALITDGPGGSKWMYVGKKHAGKV
SEQ ID NO 5  (398) QRDYIDHQDIIGWTREGIDSKPNSGLAALITDGPGGSKWMYVGKKHAGKV
SEQ ID NO 7  (399) QHDYLDHSDIIGWTREGVTEKPGSGLAALITDGPGGSKWMYVGKQHAGKV 451                                             500
SEQ ID NO 1  (449) FYDLTGNRSDTVTINSDGWGEFKVNGGSVSVWVPRKTTVSTIARPI---T
SEQ ID NO 2  (448) FYDLTGNRSDTVTINADGWGEFKVNGGSVSIWVPKISTTSQITFTVNNAT
SEQ ID NO 3  (450) FYDLTGNRSDTVTINADGWGEFKVNGGSVSIWVPKTSTTSQITFTVNNAT
SEQ ID NO 4  (451) FYDLTGNRSDTVTINADGWGEFKVNGGSVSIWVAKT---SNVTFTVNNAT
SEQ ID NO 5  (448) FYDLTGNRSDTVTINADGWGEFKVNGGSVSIWVAKT---SQVTFTVNNAT
SEQ ID NO 7  (449) FYDLTGNRSDTVTINSDGWGEFKVNGGSVSVWVPRKTT------------

501                                             550
SEQ ID NO 1  (496) TRPWTGEFVRWTEPRLVAWP------------------------------
SEQ ID NO 2  (498) TVWGQNVYVVGNISQLGNWDPVHAVQMTPSSYPTWTVTIPLLQGQNIQFK
SEQ ID NO 3  (500) TVWGQNVYVVGNISQLGNWDPVNAVQMTPSSYPTWVVTVPLPQSQNIQFK
SEQ ID NO 4  (498) TTSGQNVYVVANIPELGNWNTANAIKMNPSSYPTWKATIALPQGKAIEFK
SEQ ID NO 5  (495) TISGQNVYVVGNIPELGNWNTANAIKMTPSSYPTWKATIALPQGKAIEFK
SEQ ID NO 7  (487) --------------------------------------------------

551                      587
SEQ ID NO 1  (516) -------------------------------------
SEQ ID NO 2  (548) FIKKDSAGNVIWEDISNRTYTVPTAASGAYTASWNVP
SEQ ID NO 3  (550) FIKKDGSGNVIWENISNRTYTVPTAASGAYTANWNVP
SEQ ID NO 4  (548) FIKKDQAGNVIWESTSNRTYTVPFSSTGSYTASWNVP
SEQ ID NO 5  (545) FIKKDQSGNVVWESIPNRTYTVPFLSTGSYTASWNVP
SEQ ID NO 7  (487) -------------------------------------
```

Fig. 1(b)

SEQUENCE LISTING

```
<160> NUMBER OF SEQ ID NOS: 7

<210> SEQ ID NO 1
<211> LENGTH: 515
<212> TYPE: PRT
<213> ORGANISM: Bacillus stearothermophilus

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125
```

```
Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 2
<211> LENGTH: 584
<212> TYPE: PRT
```

<213> ORGANISM: Bacillus flavothermus

<400> SEQUENCE: 2

```
Val Pro Val Asn Gly Thr Met Met Gln Tyr Phe Glu Trp Tyr Leu Pro
1               5                   10                  15
Asp Asp Gly Thr Leu Trp Thr Lys Val Ala Asn Asn Ala Gln Ser Leu
            20                  25                  30
Ala Asn Leu Gly Ile Thr Ala Leu Trp Leu Pro Pro Ala Tyr Lys Gly
        35                  40                  45
Thr Ser Ser Ser Asp Val Gly Tyr Gly Val Tyr Asp Leu Tyr Asp Leu
    50                  55                  60
Gly Glu Phe Asn Gln Lys Gly Thr Val Arg Thr Lys Tyr Gly Thr Lys
65                  70                  75                  80
Thr Gln Tyr Ile Gln Ala Ile Gln Ala Ala His Thr Ala Gly Met Gln
                85                  90                  95
Val Tyr Ala Asp Val Val Phe Asn His Lys Ala Gly Ala Asp Gly Thr
            100                 105                 110
Glu Leu Val Asp Ala Val Glu Val Asn Pro Ser Asp Arg Asn Gln Glu
        115                 120                 125
Ile Ser Gly Thr Tyr Gln Ile Gln Ala Trp Thr Lys Phe Asp Phe Pro
    130                 135                 140
Gly Arg Gly Asn Thr Tyr Ser Ser Phe Lys Trp Arg Trp Tyr His Phe
145                 150                 155                 160
Asp Gly Thr Asp Trp Asp Glu Ser Arg Lys Leu Asn Arg Ile Tyr Lys
                165                 170                 175
Phe Arg Gly Thr Gly Lys Ala Trp Asp Trp Glu Val Asp Thr Glu Asn
            180                 185                 190
Gly Asn Tyr Asp Tyr Leu Met Tyr Ala Asp Leu Asp Met Asp His Pro
        195                 200                 205
Glu Val Val Ser Glu Leu Lys Asn Trp Gly Lys Trp Tyr Val Thr Thr
    210                 215                 220
Thr Asn Ile Asp Gly Phe Arg Leu Asp Ala Val Lys His Ile Lys Tyr
225                 230                 235                 240
Ser Phe Phe Pro Asp Trp Leu Ser Tyr Val Arg Thr Gln Thr Gln Lys
                245                 250                 255
Pro Leu Phe Ala Val Gly Glu Phe Trp Ser Tyr Asp Ile Ser Lys Leu
            260                 265                 270
His Asn Tyr Ile Thr Lys Thr Asn Gly Ser Met Ser Leu Phe Asp Ala
        275                 280                 285
Pro Leu His Asn Asn Phe Tyr Ile Ala Ser Lys Ser Gly Gly Tyr Phe
    290                 295                 300
Asp Met Arg Thr Leu Leu Asn Asn Thr Leu Met Lys Asp Gln Pro Thr
305                 310                 315                 320
Leu Ala Val Thr Leu Val Asp Asn His Asp Thr Glu Pro Gly Gln Ser
                325                 330                 335
Leu Gln Ser Trp Val Glu Pro Trp Phe Lys Pro Leu Ala Tyr Ala Phe
            340                 345                 350
Ile Leu Thr Arg Gln Glu Gly Tyr Pro Cys Val Phe Tyr Gly Asp Tyr
        355                 360                 365
Tyr Gly Ile Pro Lys Tyr Asn Ile Pro Ala Leu Lys Ser Lys Leu Asp
    370                 375                 380
Pro Leu Leu Ile Ala Arg Arg Asp Tyr Ala Tyr Gly Thr Gln His Asp
385                 390                 395                 400
```

```
Tyr Ile Asp Ser Ala Asp Ile Ile Gly Trp Thr Arg Glu Gly Val Ala
                405                 410                 415

Glu Lys Ala Asn Ser Gly Leu Ala Ala Leu Ile Thr Asp Gly Pro Gly
            420                 425                 430

Gly Ser Lys Trp Met Tyr Val Gly Lys Gln His Ala Gly Lys Thr Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Ser Val Ser Ile Trp Val
465                 470                 475                 480

Pro Lys Ile Ser Thr Ser Gln Ile Thr Phe Thr Val Asn Asn Ala
                485                 490                 495

Thr Thr Val Trp Gly Gln Asn Val Tyr Val Val Gly Asn Ile Ser Gln
                500                 505                 510

Leu Gly Asn Trp Asp Pro Val His Ala Val Gln Met Thr Pro Ser Ser
            515                 520                 525

Tyr Pro Thr Trp Thr Val Thr Ile Pro Leu Leu Gln Gly Gln Asn Ile
        530                 535                 540

Gln Phe Lys Phe Ile Lys Lys Asp Ser Ala Gly Asn Val Ile Trp Glu
545                 550                 555                 560

Asp Ile Ser Asn Arg Thr Tyr Thr Val Pro Thr Ala Ala Ser Gly Ala
                565                 570                 575

Tyr Thr Ala Ser Trp Asn Val Pro
            580

<210> SEQ ID NO 3
<211> LENGTH: 586
<212> TYPE: PRT
<213> ORGANISM: bacillus

<400> SEQUENCE: 3

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190
```

Glu Asn Gly Asn Tyr Asp Tyr Leu Met Tyr Ala Asp Leu Asp Met Asp
            195                 200                 205

His Pro Glu Val Val Ser Glu Leu Lys Asn Trp Gly Lys Trp Tyr Val
    210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
    290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Val Gly Asn Ile
            500                 505                 510

Ser Gln Leu Gly Asn Trp Asp Pro Val Asn Ala Val Gln Met Thr Pro
        515                 520                 525

Ser Ser Tyr Pro Thr Trp Val Val Thr Val Pro Leu Pro Gln Ser Gln
    530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
            580                 585

<210> SEQ ID NO 4
<211> LENGTH: 583

<212> TYPE: PRT
<213> ORGANISM: bacillus

<400> SEQUENCE: 4

```
Asn Thr Ala Pro Ile Asn Glu Thr Met Met Gln Tyr Phe Glu Trp Asp
1               5                   10                  15
Leu Pro Asn Asp Gly Thr Leu Trp Thr Lys Val Lys Asn Glu Ala Ala
            20                  25                  30
Asn Leu Ser Ser Leu Gly Ile Thr Ala Leu Trp Leu Pro Pro Ala Tyr
        35                  40                  45
Lys Gly Thr Ser Gln Ser Asp Val Gly Tyr Gly Val Tyr Asp Leu Tyr
50                  55                  60
Asp Leu Gly Glu Phe Asn Gln Lys Gly Thr Ile Arg Thr Lys Tyr Gly
65                  70                  75                  80
Thr Lys Thr Gln Tyr Ile Gln Ala Ile Gln Ala Lys Ala Ala Gly
                85                  90                  95
Met Gln Val Tyr Ala Asp Val Val Phe Asn His Lys Ala Gly Ala Asp
            100                 105                 110
Gly Thr Glu Phe Val Asp Ala Val Glu Val Asp Pro Ser Asn Arg Asn
        115                 120                 125
Gln Glu Thr Ser Gly Thr Tyr Gln Ile Gln Ala Trp Thr Lys Phe Asp
130                 135                 140
Phe Pro Gly Arg Gly Asn Thr Tyr Ser Ser Phe Lys Trp Arg Trp Tyr
145                 150                 155                 160
His Phe Asp Gly Thr Asp Trp Asp Glu Ser Arg Lys Leu Asn Arg Ile
                165                 170                 175
Tyr Lys Phe Arg Ser Thr Gly Lys Ala Trp Asp Trp Glu Val Asp Thr
            180                 185                 190
Glu Asn Gly Asn Tyr Asp Tyr Leu Met Phe Ala Asp Leu Asp Met Asp
        195                 200                 205
His Pro Glu Val Val Thr Glu Leu Lys Asn Trp Gly Thr Trp Tyr Val
210                 215                 220
Asn Thr Thr Asn Ile Asp Gly Phe Arg Leu Asp Ala Val Lys His Ile
225                 230                 235                 240
Lys Tyr Ser Phe Phe Pro Asp Trp Leu Thr Tyr Val Arg Asn Gln Thr
                245                 250                 255
Gly Lys Asn Leu Phe Ala Val Gly Glu Phe Trp Ser Tyr Asp Val Asn
            260                 265                 270
Lys Leu His Asn Tyr Ile Thr Lys Thr Asn Gly Ser Met Ser Leu Phe
        275                 280                 285
Asp Ala Pro Leu His Asn Asn Phe Tyr Thr Ala Ser Lys Ser Ser Gly
290                 295                 300
Tyr Phe Asp Met Arg Tyr Leu Leu Asn Asn Thr Leu Met Lys Asp Gln
305                 310                 315                 320
Pro Ser Leu Ala Val Thr Leu Val Asp Asn His Asp Thr Gln Pro Gly
                325                 330                 335
Gln Ser Leu Gln Ser Trp Val Glu Pro Trp Phe Lys Pro Leu Ala Tyr
            340                 345                 350
Ala Phe Ile Leu Thr Arg Gln Glu Gly Tyr Pro Cys Val Phe Tyr Gly
        355                 360                 365
Asp Tyr Tyr Gly Ile Pro Lys Tyr Asn Ile Pro Gly Leu Lys Ser Lys
370                 375                 380
Ile Asp Pro Leu Leu Ile Ala Arg Arg Asp Tyr Ala Tyr Gly Thr Gln
385                 390                 395                 400
```

```
Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
            485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
            515                 520                 525

Pro Thr Trp Lys Ala Thr Ile Ala Leu Pro Gln Gly Lys Ala Ile Glu
            530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
            565                 570                 575

Thr Ala Ser Trp Asn Val Pro
            580

<210> SEQ ID NO 5
<211> LENGTH: 583
<212> TYPE: PRT
<213> ORGANISM: bacillus

<400> SEQUENCE: 5

Asn Thr Ala Pro Val Asn Gly Thr Met Met Gln Tyr Phe Glu Trp Asp
1               5                   10                  15

Leu Pro Asn Asp Gly Thr Leu Trp Thr Lys Val Lys Asn Glu Ala Ser
            20                  25                  30

Ser Leu Ser Ser Leu Gly Ile Thr Ala Leu Trp Leu Pro Pro Ala Tyr
        35                  40                  45

Lys Gly Thr Ser Gln Gly Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Leu Gln Ala Ile Gln Ala Ala Lys Ser Ala Gly
                85                  90                  95

Met Gln Val Tyr Ala Asp Val Val Phe Asn His Lys Ala Gly Ala Asp
            100                 105                 110

Ser Thr Glu Trp Val Asp Ala Val Glu Val Asn Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
```

```
            180                 185                 190
Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
210                 215                 220

Asn Thr Thr Asn Val Asp Gly Phe Arg Leu Asp Ala Val Lys His Ile
225                 230                 235                 240

Lys Tyr Ser Phe Phe Pro Asp Trp Leu Thr His Val Arg Ser Gln Thr
            245                 250                 255

Arg Lys Asn Leu Phe Ala Val Gly Glu Phe Trp Ser Tyr Asp Val Asn
            260                 265                 270

Lys Leu His Asn Tyr Ile Thr Lys Thr Ser Gly Thr Met Ser Leu Phe
            275                 280                 285

Asp Ala Pro Leu His Asn Phe Tyr Thr Ala Ser Lys Ser Ser Gly
            290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
            325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Ser Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Gln Val Thr Phe Thr Val Asn Asn Ala Thr
            485                 490                 495

Thr Ile Ser Gly Gln Asn Val Tyr Val Val Gly Asn Ile Pro Glu Leu
            500                 505                 510

Gly Asn Trp Asn Thr Ala Asn Ala Ile Lys Met Thr Pro Ser Ser Tyr
            515                 520                 525

Pro Thr Trp Lys Ala Thr Ile Ala Leu Pro Gln Gly Lys Ala Ile Glu
            530                 535                 540

Phe Lys Phe Ile Lys Lys Asp Gln Ser Gly Asn Val Val Trp Glu Ser
545                 550                 555                 560

Ile Pro Asn Arg Thr Tyr Thr Val Pro Phe Leu Ser Thr Gly Ser Tyr
            565                 570                 575

Thr Ala Ser Trp Asn Val Pro
            580

<210> SEQ ID NO 6
```

```
<211> LENGTH: 491
<212> TYPE: PRT
<213> ORGANISM: Artificial sequence
<220> FEATURE:
<223> OTHER INFORMATION: Synthetic construct

<400> SEQUENCE: 6
```

| | | | | | | | | | | | | | | | |
|---|---|---|---|---|---|---|---|---|---|---|---|---|---|---|---|
| Ala | Ala | Pro | Phe | Asn | Gly | Thr | Met | Met | Gln | Tyr | Phe | Glu | Trp | Tyr | Leu |
| 1 | | | | 5 | | | | | 10 | | | | | 15 | |
| Pro | Asp | Asp | Gly | Thr | Leu | Trp | Thr | Lys | Val | Ala | Asn | Glu | Ala | Asn | Asn |
| | | | 20 | | | | | 25 | | | | | 30 | | |
| Leu | Ser | Ser | Leu | Gly | Ile | Thr | Ala | Leu | Trp | Leu | Pro | Ala | Tyr | Lys | |
| | | 35 | | | | | 40 | | | | | 45 | | | |
| Gly | Thr | Ser | Arg | Ser | Asp | Val | Gly | Tyr | Gly | Val | Tyr | Asp | Leu | Tyr | Asp |
| | 50 | | | | | 55 | | | | | 60 | | | | |
| Leu | Gly | Glu | Phe | Asn | Gln | Lys | Gly | Thr | Val | Arg | Thr | Lys | Tyr | Gly | Thr |
| 65 | | | | | 70 | | | | | 75 | | | | | 80 |
| Lys | Ala | Gln | Tyr | Leu | Gln | Ala | Ile | Gln | Ala | Ala | His | Ala | Ala | Gly | Met |
| | | | | 85 | | | | | 90 | | | | | 95 | |
| Gln | Val | Tyr | Ala | Asp | Val | Val | Phe | Asp | His | Lys | Gly | Gly | Ala | Asp | Gly |
| | | | 100 | | | | | 105 | | | | | 110 | | |
| Thr | Glu | Trp | Val | Asp | Ala | Val | Glu | Val | Asn | Pro | Ser | Asp | Arg | Asn | Gln |
| | | 115 | | | | | 120 | | | | | 125 | | | |
| Glu | Ile | Ser | Gly | Thr | Tyr | Gln | Ile | Gln | Ala | Trp | Thr | Lys | Phe | Asp | Phe |
| | 130 | | | | | 135 | | | | | 140 | | | | |
| Pro | Gly | Arg | Gly | Asn | Thr | Tyr | Ser | Ser | Phe | Lys | Trp | Arg | Trp | Tyr | His |
| 145 | | | | | 150 | | | | | 155 | | | | | 160 |
| Phe | Asp | Gly | Val | Asp | Trp | Asp | Glu | Ser | Arg | Lys | Leu | Ser | Arg | Ile | Tyr |
| | | | | 165 | | | | | 170 | | | | | 175 | |
| Lys | Phe | Arg | Gly | Lys | Ala | Trp | Asp | Trp | Glu | Val | Asp | Thr | Glu | Phe | Gly |
| | | | 180 | | | | | 185 | | | | | 190 | | |
| Asn | Tyr | Asp | Tyr | Leu | Met | Tyr | Ala | Asp | Leu | Asp | Met | Asp | His | Pro | Glu |
| | | 195 | | | | | 200 | | | | | 205 | | | |
| Val | Val | Thr | Glu | Leu | Lys | Asn | Trp | Gly | Lys | Trp | Tyr | Val | Asn | Thr | Thr |
| | 210 | | | | | 215 | | | | | 220 | | | | |
| Asn | Ile | Asp | Gly | Phe | Arg | Leu | Asp | Ala | Val | Lys | His | Ile | Lys | Phe | Ser |
| 225 | | | | | 230 | | | | | 235 | | | | | 240 |
| Phe | Phe | Pro | Asp | Trp | Leu | Ser | Tyr | Val | Arg | Ser | Gln | Thr | Gly | Lys | Pro |
| | | | | 245 | | | | | 250 | | | | | 255 | |
| Leu | Phe | Thr | Val | Gly | Glu | Tyr | Trp | Ser | Tyr | Asp | Ile | Asn | Lys | Leu | His |
| | | | 260 | | | | | 265 | | | | | 270 | | |
| Asn | Tyr | Ile | Thr | Lys | Thr | Asp | Gly | Thr | Met | Ser | Leu | Phe | Asp | Ala | Pro |
| | | 275 | | | | | 280 | | | | | 285 | | | |
| Leu | His | Asn | Lys | Phe | Tyr | Thr | Ala | Ser | Lys | Ser | Gly | Gly | Ala | Phe | Asp |
| | 290 | | | | | 295 | | | | | 300 | | | | |
| Met | Arg | Thr | Leu | Met | Thr | Asn | Thr | Leu | Met | Lys | Asp | Gln | Pro | Thr | Leu |
| 305 | | | | | 310 | | | | | 315 | | | | | 320 |
| Ala | Val | Thr | Phe | Val | Asp | Asn | His | Asp | Thr | Glu | Pro | Gly | Gln | Ala | Leu |
| | | | | 325 | | | | | 330 | | | | | 335 | |
| Gln | Ser | Trp | Val | Asp | Pro | Trp | Phe | Lys | Pro | Leu | Ala | Tyr | Ala | Phe | Ile |
| | | | 340 | | | | | 345 | | | | | 350 | | |
| Leu | Thr | Arg | Gln | Glu | Gly | Tyr | Pro | Cys | Val | Phe | Tyr | Gly | Asp | Tyr | Tyr |
| | | 355 | | | | | 360 | | | | | 365 | | | |
| Gly | Ile | Pro | Gln | Tyr | Asn | Ile | Pro | Ser | Leu | Lys | Ser | Lys | Ile | Asp | Pro |
| | 370 | | | | | 375 | | | | | 380 | | | | |

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
            405                 410                 415

Lys Pro Gly Ser Gly Leu Ala Ala Leu Ile Thr Asp Gly Pro Gly Gly
        420                 425                 430

Ser Lys Trp Met Tyr Val Gly Lys Gln His Ala Gly Lys Val Phe Tyr
    435                 440                 445

Asp Leu Thr Gly Asn Arg Ser Asp Thr Val Thr Ile Asn Ser Asp Gly
450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
                485                 490

<210> SEQ ID NO 7
<211> LENGTH: 486
<212> TYPE: PRT
<213> ORGANISM: Bacillus stearothermophilus

<400> SEQUENCE: 7

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys

```
                260                   265                   270
Leu His Asn Tyr Ile Thr Lys Thr Asn Gly Thr Met Ser Leu Phe Asp
            275                   280                   285

Ala Pro Leu His Asn Lys Phe Tyr Thr Ala Ser Lys Ser Gly Gly Ala
        290                   295                   300

Phe Asp Met Arg Thr Leu Met Thr Asn Thr Leu Met Lys Asp Gln Pro
305                   310                   315                   320

Thr Leu Ala Val Thr Phe Val Asp Asn His Asp Thr Glu Pro Gly Gln
                325                   330                   335

Ala Leu Gln Ser Trp Val Asp Pro Trp Phe Lys Pro Leu Ala Tyr Ala
            340                   345                   350

Phe Ile Leu Thr Arg Gln Glu Gly Tyr Pro Cys Val Phe Tyr Gly Asp
        355                   360                   365

Tyr Tyr Gly Ile Pro Gln Tyr Asn Ile Pro Ser Leu Lys Ser Lys Ile
    370                   375                   380

Asp Pro Leu Leu Ile Ala Arg Arg Asp Tyr Ala Tyr Gly Thr Gln His
385                   390                   395                   400

Asp Tyr Leu Asp His Ser Asp Ile Ile Gly Trp Thr Arg Glu Gly Val
                405                   410                   415

Thr Glu Lys Pro Gly Ser Gly Leu Ala Ala Leu Ile Thr Asp Gly Pro
            420                   425                   430

Gly Gly Ser Lys Trp Met Tyr Val Gly Lys Gln His Ala Gly Lys Val
            435                   440                   445

Phe Tyr Asp Leu Thr Gly Asn Arg Ser Asp Thr Val Thr Ile Asn Ser
        450                   455                   460

Asp Gly Trp Gly Glu Phe Lys Val Asn Gly Gly Ser Val Ser Val Trp
465                   470                   475                   480

Val Pro Arg Lys Thr Thr
            485
```

ALPHA-AMYLASE VARIANTS AND POLYNUCLEOTIDES ENCODING SAME

CROSS-REFERENCE TO RELATED APPLICATIONS

This application is a 35 U.S.C. 371 national application of PCT/US2011/020128 filed Jan. 4, 2011, which claims priority or the benefit under 35 U.S.C. 119 of European application nos. 10150063.5 and 10150062.7 both filed Jan. 4, 2010 and U.S. provisional application Nos. 61/292,324, 61/292,327 61/304,092, 61/333,930, 61/354,775, 61/354,817, 61/355,230 and 61/362,536 filed Jan. 5, 2010, Jan. 5, 2010, Feb. 12, 2010, May 12, 2010, Jun. 15, 2010, Jun. 15, 2010, Jun. 16, 2010 and Jul. 8, 2010, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to alpha-amylase variants having an improved property, e.g., improved stability, polynucleotides encoding the variants, methods of producing the variants, and methods of using the variants.

2. Description of the Related Art

Alpha-amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

Alpha-amylases are used commercially for a variety of purposes such as in the initial stages of starch processing (e.g., liquefaction); in wet milling processes; and in alcohol production from carbohydrate sources. They are also used as cleaning agents or adjuncts in detergent matrices; in the textile industry for starch desizing; in baking applications; in the beverage industry; in oil fields in drilling processes; in recycling processes, e.g., for de-inking paper; and in animal feed.

SUMMARY OF THE INVENTION

The present invention provides alpha-amylase variants with improved properties, e.g., improved thermostability, compared to their parent enzyme.

The present invention relates to isolated variants of a parent alpha-amylase, comprising a substitution at three or more (several) positions corresponding to positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

The present invention also relates to isolated polynucleotides encoding an alpha-amylase variant, nucleic acid constructs, vectors, and host cells comprising the polynucleotides, and methods of producing a variant of a parent alpha-amylase.

The present invention also relates to the use of the variants in starch processing (e.g., liquefaction); wet milling processes; alcohol production from carbohydrate sources; detergents; dishwashing compositions; starch desizing in the textile industry; baking applications; the beverage industry; oil fields in drilling processes; recycling processes, e.g., for de-inking paper, and animal feed.

BRIEF DESCRIPTION OF THE FIGURES

FIGS. 1(a)-(b) show an alignment of the catalytic domains of alpha-amylases with the amino acid sequence of SEQ ID NOs: 1, 2, 3, 4, 5 and 7. SEQ ID NO: 1 is a *Bacillus stearothermophilus* alpha-amylase; SEQ ID NO: 2 is *Bacillus flavothermus* amylase, AMY1048 described in WO 2005/001064; SEQ ID NO: 3 is the *Bacillus* alpha-amylase TS-22; SEQ ID NO:4 is the *Bacillus* alpha-amylase TS-23 described in J. Appl. Microbiology, 1997, 82: 325-334 (SWALL: q59222); SEQ ID NO: 5 is an alpha-amylase described in WO 2004/091544; and SEQ ID NO: 7 is another *Bacillus stearothermophilus* alpha-amylase.

DETAILED DESCRIPTION OF THE INVENTION

The present invention relates to isolated variants of a parent alpha-amylase, comprising a substitution at three or more (several) positions corresponding to positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, wherein the variant has at least 65% and less than 100% sequence identity with at least one of the mature polypeptide of SEQ ID NO: 1; and the variant has alpha-amylase activity.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylases (alpha-1,4-glucan-4-glucanohydrolases, E.C. 3.2.1.1) are a group of enzymes, which catalyze the hydrolysis of starch and other linear and branched 1,4-glucosidic oligo- and polysaccharides.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide of the present invention and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent alpha-amylase. Such improved properties include, but are not limited to, altered temperature-dependent activity profile, thermostability, pH activity, pH stability, substrate specificity, product specificity, and chemical stability.

Isolated variant: The terms "isolated" and "purified" mean a polypeptide or polynucleotide that is removed from at least one component with which it is naturally associated. For example, a variant may be at least 1% pure, e.g., at least 5% pure, at least 10% pure, at least 20% pure, at least 40% pure, at least 60% pure, at least 80% pure, and at least 90% pure, as determined by SDS-PAGE and a polynucleotide may be at least 1% pure, e.g., at least 5% pure, at least 10% pure, at least 20% pure, at least 40% pure, at least 60% pure, at least 80% pure, and at least 90% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 483, 1 to 486, or 1 to 493 of SEQ ID NO: 1. It is known in the art that a host cell may produce a mixture of two or more different mature polypeptides (i.e., with a different C-terminal and/or N-terminal amino acid) expressed by the same polynucleotide.

Mature polypeptide coding sequence: The term "mature polypeptide coding sequence" means a nucleotide sequence that encodes a mature polypeptide having alpha-amylase activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Operably linked: The term "operably linked" means a configuration in which a control sequence is placed at an appropriate position relative to the coding sequence of the polynucleotide sequence such that the control sequence directs the expression of the coding sequence of a polypeptide.

Parent: The term "parent" alpha-amylase means an alpha-amylase to which an alteration is made to produce a variant of the present invention. The parent may be a naturally occurring (wild-type) polypeptide or a variant thereof, prepared by suitable means. The parent may also be an allelic variant.

Polypeptide fragment: The term "polypeptide fragment" means a polypeptide having one or more (several) amino acids deleted from the amino and/or carboxyl terminus of a mature polypeptide; wherein the fragment has alpha-amylase activity. In one aspect, a fragment contains at least 483 amino acid residues, e.g., at least 486 and at least 493 amino acid residues, of the mature polypeptide of SEQ ID NO: 1.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide sequence having one or more (several) nucleotides deleted from the 5' and/or 3' end of a mature polypeptide coding sequence; wherein the subsequence encodes a polypeptide fragment having alpha-amylase activity.

Variant: The term "variant" means a polypeptide having alpha-amylase activity comprising an alteration, i.e., a substitution, insertion, and/or deletion, of one or more (several) amino acid residues at one or more (several) positions. A substitution means a replacement of an amino acid occupying a position with a different amino acid; a deletion means removal of an amino acid occupying a position; and an insertion means adding 1-5 amino acids adjacent to and following an amino acid occupying a position.

Wild-Type: The term "wild-type" means an alpha-amylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1 can be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another alpha-amylase can be confirmed by an alignment of multiple polypeptide sequences using "ClustalW" (Larkin et al., 2007, *Bioinformatics* 23: 2947-2948).

When the other enzyme has diverged from the mature polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more (several) representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Eng.* 11: 739-747), and implementations of these algorithms can additionally be utilized to query structure databases with a structure of interest in order to discover possible structural homologs (e.g., Holm and Park, 2000, *Bioinformatics* 16: 566-567). These structural alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the alpha-amylase variants of the present invention, the nomenclature described below is adapted for ease of reference. In all cases, the accepted IUPAC single letter or triple letter amino acid abbreviation is employed.

Substitutions. For an amino acid substitution, the following nomenclature is used: original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequence would thus be:

| Parent: | Variant: |
|---------|----------|
| 195     | 195 195a 195b |
| G       | G-K-A    |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different alterations. Where different alterations can be introduced at a position, the different alterations are separated by a comma, e.g., "Arg170Tyr,Glu" represents a substitution of arginge with tyrosine or glutamic acid at position 170. Thus, "Tyr167Gly,Ala+Arg170Gly,Ala" designates the following variants:
Tyr167Gly+Arg170Gly, Tyr167Gly+Arg170Ala, Tyr167Ala+Arg170Gly, and Tyr167Ala+Arg170Ala.

Parent Alpha-Amylases

In a first aspect, the parent alpha-amylase has a sequence identity to the mature polypeptide of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%.

In a second aspect, the parent alpha-amylase has a sequence identity to the mature polypeptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%.

In a third aspect, the parent alpha-amylase has a sequence identity to the mature polypeptide of SEQ ID NO: 3 of at least 60%, e.g., at least 65%, at least 70%, at least 75%, at least 80%, at least 85%, at least 90%, at least 95%, at least 96%, at least 97%, at least 98%, at least 99%, or 100%.

In a fourth aspect, the parent alpha-amylase has a sequence identity to the mature polypeptide of SEQ ID NO: 4 of at least 60%, e.g., at least 65%, at least 70%, at least 75%, at least 80%, at least 85%, at least 90%, at least 95%, at least 96%, at least 97%, at least 98%, at least 99%, or 100%.

In a fifth aspect, the parent alpha-amylase has a sequence identity to the mature polypeptide of SEQ ID NO: 5 of at least 60%, e.g., at least 65%, at least 70%, at least 75%, at least 80%, at least 85%, at least 90%, at least 95%, at least 96%, at least 97%, at least 98%, at least 99%, or 100%.

In a sixth aspect, the parent alpha-amylase has a sequence identity to the mature polypeptide of SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100%.

In a seventh aspect, the parent alpha-amylase has a sequence identity to the mature polypeptide of SEQ ID NO: 7 of at least 60%, e.g., at least 65%, at least 70%, at least 75%, at least 80%, at least 85%, at least 90%, at least 95%, at least 96%, at least 97%, at least 98%, at least 99%, or 100%.

The parent alpha-amylase preferably comprises the amino acid sequence of SEQ ID NO: 1. In another aspect, the parent alpha-amylase comprises or consists of the mature polypeptide of SEQ ID NO: 1. In another aspect, the parent alpha-amylase comprises or consists of amino acids 1 to 486 or amino acids 1 to 493 of SEQ ID NO: 1.

The parent alpha-amylase preferably comprises the amino acid sequence of SEQ ID NO: 2. In another aspect, the parent alpha-amylase comprises or consists of the mature polypeptide of SEQ ID NO: 2. In another aspect, the parent alpha-amylase comprises or consists of amino acids 1 to 482 of SEQ ID NO: 2. Amino acids 483-584 of SEQ ID NO: 2 represent a CBM20 binding domain.

The parent alpha-amylase preferably comprises the amino acid sequence of SEQ ID NO: 3. In another aspect, the parent alpha-amylase comprises or consists of the mature polypeptide of SEQ ID NO: 3. In another aspect, the parent alpha-amylase comprises or consists of amino acids 1 to 484 of SEQ ID NO: 3. Amino acids 485-586 of SEQ ID NO: 3 represent a CBM20 binding domain.

The parent alpha-amylase preferably comprises the amino acid sequence of SEQ ID NO: 4. In another aspect, the parent alpha-amylase comprises or consists of the mature polypeptide of SEQ ID NO: 4. In another aspect, the parent alpha-amylase comprises or consists of amino acids 1 to 484 of SEQ ID NO: 4. Amino acids 485-583 of SEQ ID NO: 4 represent a CBM20 binding domain.

The parent alpha-amylase preferably comprises the amino acid sequence of SEQ ID NO: 5. In another aspect, the parent alpha-amylase comprises or consists of the mature polypeptide of SEQ ID NO: 5. In another aspect, the parent alpha-amylase comprises or consists of amino acids 1 to 484 of SEQ ID NO: 5. Amino acids 485-583 of SEQ ID NO: 5 represent a CBM20 binding domain.

The parent alpha-amylase preferably comprises or consists of the amino acid sequence of SEQ ID NO: 6.

The parent alpha-amylase preferably comprises the amino acid sequence of SEQ ID NO: 7. In another aspect, the parent alpha-amylase comprises or consists of the mature polypeptide of SEQ ID NO: 7. In another aspect, the parent alpha-amylase comprises or consists of amino acids 1 to 486 of SEQ ID NO: 7.

In an embodiment, the parent alpha-amylase is a fragment of the mature polypeptide of SEQ ID NO: 1 containing at least 483 amino acid residues.

In an embodiment, the parent alpha-amylase is a fragment of the mature polypeptide of SEQ ID NO: 2 containing at least 482 amino acid residues.

In an embodiment, the parent alpha-amylase is a fragment of the mature polypeptide of SEQ ID NO: 3 containing at least 484 amino acid residues.

In an embodiment, the parent alpha-amylase is a fragment of the mature polypeptide of SEQ ID NO: 4 containing at least 484 amino acid residues.

In an embodiment, the parent alpha-amylase is a fragment of the mature polypeptide of SEQ ID NO: 5 containing at least 484 amino acid residues.

In an embodiment, the parent alpha-amylase is a fragment of the mature polypeptide of SEQ ID NO: 6 containing at least 486 amino acid residues.

In an embodiment, the parent alpha-amylase is a fragment of the mature polypeptide of SEQ ID NO: 7 containing at least 486 amino acid residues.

In another embodiment, the parent enzyme is an allelic variant of the mature polypeptide of SEQ ID NO: 1.

In another embodiment, the parent enzyme is an allelic variant of the mature polypeptide of SEQ ID NO: 2.

In another embodiment, the parent enzyme is an allelic variant of the mature polypeptide of SEQ ID NO: 3.

In another embodiment, the parent enzyme is an allelic variant of the mature polypeptide of SEQ ID NO: 4.

In another embodiment, the parent enzyme is an allelic variant of the mature polypeptide of SEQ ID NO: 5.

In another embodiment, the parent enzyme is an allelic variant of the mature polypeptide of SEQ ID NO: 6.

In another embodiment, the parent enzyme is an allelic variant of the mature polypeptide of SEQ ID NO: 7.

The parent alpha-amylase may be obtained from microorganisms of any genus. For purposes of the present invention, the term "obtained from" as used herein in connection with a given source shall mean that the parent alpha-amylase encoded by a polynucleotide is produced by the source or by a cell in which the polynucleotide from the source has been inserted. In one aspect, the parent alpha-amylase is secreted extracellularly.

The parent alpha-amylase may be a bacterial alpha-amylase. For example, the alpha-amylase may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* alpha-amylase, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasman* alpha-amylase.

In one aspect, the parent alpha-amylase is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* alpha-aylase.

In another aspect, the parent alpha-amylase is a *Streptococcus equisimilis, Streptococcus pyogenes, Streptococcus uberis*, or *Streptococcus equi* subsp. *Zooepidemicus* alpha-amylase.

In another aspect, the polypeptide is a *Streptomyces achromogenes, Streptomyces avermitilis, Streptomyces coelicolor, Streptomyces griseus*, or *Streptomyces lividans* alpha-amylase.

The parent alpha-amylase may be a fungal alpha-amylase. In another aspect, the fungal alpha-amylase is a yeast alpha-amylase such as a *Candida, Kluyveromyces, Pichia, Saccharomyces, Schizosaccharomyces*, or *Yarrowia* alpha-amylase. In another aspect, the fungal alpha-amylase is a filamentous fungal alpha-amylase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus,*

*Dyphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* alpha-amylase.

In another aspect, the parent alpha-amylase is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* alpha-amylase.

In another aspect, the parent alpha-amylase is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* alpha-amylase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent alpha-amylase may also be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding an alpha-amylase may then be derived by similarly screening a genomic or cDNA library of another microorganism or mixed DNA sample. Once a polynucleotide encoding an alpha-amylase has been detected with suitable probe(s) as described herein, the sequence may be isolated or cloned by utilizing techniques that are known to those of ordinary skill in the art (see, e.g., Sambrook et al., 1989, supra).

The parent alpha-amylase can also include hybrid polypeptides in which a portion of one polypeptide is fused at the N-terminus or the C-terminus of a portion of another polypeptide.

The parent alpha-amylase can also include fused polypeptides or cleavable fusion polypeptides in which one polypeptide is fused at the N-terminus or the C-terminus of another polypeptide. A fused polypeptide is produced by fusing a polynucleotide (or a portion thereof) encoding another polypeptide to a polynucleotide (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site. Upon secretion of the fusion protein, the site is cleaved releasing the variant from the fusion protein. Examples of cleavage sites include, but are not limited to, the cleavage sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; Contreras et al., 1991, *Biotechnology* 9: 378-381; Eaton et al., 1986, *Biochem.* 25: 505-512); Collins-Racie et al., 1995, *Biotechnology* 13: 982-987; Carter et al., 1989, *Proteins: Structure, Function, and Genetics* 6: 240-248); and Stevens, 2003, *Drug Discovery World* 4: 35-48.

Preparation of Variants

The present invention also relates to methods for obtaining a variant having alpha-amylase activity, comprising: (a) introducing into a parent alpha-amylase a substitution at three or more (several) positions corresponding to positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, wherein the variant has alpha-amylase activity; and (b) recovering the variant.

The variants can be prepared according to any mutagenesis procedure known in the art, such as site-directed mtagenesis, synthetic gene construction, semi-synthetic gene construction, random mutagenesis, shuffling, etc.

Site-directed mutagenesis is a technique in which one or more (several) mutations are created at a defined site in a polynucleotide molecule encoding the parent alpha-amylase. The technique can be performed in vitro or in vivo.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian et al., 2004, *Nature* 432: 1050-1054, and similar technologies wherein olgionucleotides are synthesized and assembled upon photo-programable microfluidic chips.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent alpha-amylase and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, for example, Scherer and Davis, 1979, *Proc. Natl. Acad. Sci. USA* 76: 4949-4955; and Barton et al., 1990, *Nucleic Acids Research* 18: 7349-4966.

Site-directed mutagenesis can be accomplished in vivo by methods known in the art. See, for example, U.S. Patent Application Publication No. 2004/0171154; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent alpha-amylase.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR ampflication. Polynucleotide fragments may then be shuffled.

Variants

The present invention relates to variants comprising a substitution at three or more (several) positions corresponding to positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, wherein the variant having alpha-amylase activity.

In an embodiment, the variant has a sequence identity of at least 65%, e.g., at least 70%, at least 75%, at least 80%, at least 85%, at least 90%, at least 95%, at least 96%, at least 97%, at least 98%, or at least 99%, but less than 100%, to the amino acid sequence of the parent alpha-amylase.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 1.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 2.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 3.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 4.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 5.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 6.

In another embodiment, the variant has a sequence identity of at least 65%, e.g., at least 70%, at least 75%, at least 80%, at least 85%, at least 90%, at least 95%, at least 96%, at least 97%, at least 98%, and at least 99%, but less than 100% with the mature polypeptide of SEQ ID NO: 7.

In an embodiment, the variant comprises a substitution at a position corresponding to position 59 with Ala, Arg, Asn, Asp, Cys, Gln, Glu, Gly, His, Ile, Leu, Lys, Met, Phe, Pro, Ser, Thr, Trp, or Tyr, in particular with Ala, Gln, Glu, Gly, Ile, Leu, Prot, or Thr.

In an embodiment, the variant comprises a substitution at a position corresponding to position 89 with Ala, Arg, Asn, Asp, Cys, Glu, Gly, His, Ile, Leu, Lys, Met, Phe, Pro, Ser, Thr, Trp, Tyr, or Val, in particular with Arg, His, or Lys.

In an embodiment, the variant comprises a substitution at a position corresponding to position 91 with Arg, Asn, Asp, Cys, Gln, Glu, Gly, His, Ile, Leu, Lys, Met, Phe, Pro, Ser, Thr, Trp, Tyr, or Val, in particular with Ile, Leu, or Val.

In an embodiment, the variant comprises a substitution at a position corresponding to position 96 with Ala, Arg, Asn, Asp, Cys, Gln, Glu, Gly, His, Ile, Leu, Lys, Phe, Pro, Ser, Thr, Trp, Tyr, or Val, in particular with Ile, Leu, or Val.

In an embodiment, the variant comprises a substitution at a position corresponding to position 108 with Ala, Arg, Asn, Asp, Cys, Gln, Glu, His, Ile, Leu, Lys, Met, Phe, Pro, Ser, Thr, Trp, Tyr, or Val, in particular with Ala.

In an embodiment, the variant comprises a substitution at a position corresponding to position 112 with Ala, Arg, Asn, Asp, Cys, Gln, Glu, His, Ile, Leu, Lys, Met, Phe, Pro, Ser, Thr, Trp, Tyr, or Val, in particular with Ala, Asp, or Glu.

In an embodiment, the variant comprises a substitution at a position corresponding to position 129 with Ala, Arg, Asn, Asp, Cys, Gln, Gly, His, Ile, Leu, Lys, Met, Phe, Pro, Ser, Thr, Trp, Tyr, or Val, in particular with Ala, Thr, or Val.

In an embodiment, the variant comprises a substitution at a position corresponding to position 157 with Ala, Asn, Asp, Cys, Gln, Glu, Gly, His, Ile, Leu, Lys, Met, Phe, Pro, Ser, Thr, Trp, Tyr, or Val, in particular with His, Lys, Phe, or Tyr.

In an embodiment, the variant comprises a substitution at a position corresponding to position 165 with Ala, Arg, Asn, Cys, Gln, Glu, Gly, His, Ile, Leu, Lys, Met, Phe, Pro, Ser, Thr, Trp, Tyr, or Val, in particular with Asn.

In an embodiment, the variant comprises a substitution at a position corresponding to position 166 with Ala, Arg, Asn, Asp, Cys, Gln, Glu, Gly, His, Ile, Leu, Lys, Met, Phe, Pro, Ser, Thr, Tyr, or Val, in particular with Phe.

In an embodiment, the variant comprises a substitution at a position corresponding to position 168 with Ala, Arg, Asn, Asp, Cys, Gln, Gly, His, Ile, Leu, Lys, Met, Phe, Pro, Ser, Thr, Trp, Tyr, or Val, in particular with Ala.

In an embodiment, the variant comprises a substitution at a position corresponding to position 171 with Ala, Arg, Asn, Asp, Cys, Gln, Glu, Gly, His, Ile, Leu, Met, Phe, Pro, Ser, Thr, Trp, Tyr, or Val, in particular with Glu.

In an embodiment, the variant comprises a substitution at a position corresponding to position 177 with Ala, Arg, Asn, Asp, Cys, Gln, Glu, Gly, His, Ile, Leu, Met, Phe, Pro, Ser, Thr, Trp, Tyr, or Val, in particular with Arg, Leu, or Met.

In an embodiment, the variant comprises a substitution at a position corresponding to position 179 with Ala, Asn, Asp, Cys, Gln, Glu, Gly, His, Ile, Leu, Lys, Met, Phe, Pro, Ser, Thr, Trp, Tyr, or Val, in particular with Gln, Glu, Ile, Leu, Lys, or Val.

In an embodiment, the variant comprises a substitution at a position corresponding to position 180 with Ala, Arg, Asn, Asp, Cys, Gln, Glu, His, Ile, Leu, Lys, Met, Phe, Pro, Ser, Thr, Trp, Tyr, or Val, in particular with Glu or Val.

In an embodiment, the variant comprises a substitution at a position corresponding to position 181 with Ala, Arg, Asn, Asp, Cys, Gln, Glu, Gly, His, Leu, Lys, Met, Phe, Pro, Ser, Thr, Trp, Tyr, or Val, in particular with Glu, Gly, or Val.

In an embodiment, the variant comprises a substitution at a position corresponding to position 184 with Arg, Asn, Asp, Cys, Gln, Glu, Gly, His, Ile, Leu, Lys, Met, Phe, Pro, Ser, Thr, Trp, Tyr, or Val, in particular with Ser.

In an embodiment, the variant comprises a substitution at a position corresponding to position 208 with Ala, Arg, Asn, Asp, Cys, Gln, Glu, Gly, Ile, Leu, Lys, Met, Phe, Pro, Ser, Thr, Trp, Tyr, or Val, in particular with Phe or Tyr.

In an embodiment, the variant comprises a substitution at a position corresponding to position 220 with Ala, Arg, Asn, Asp, Cys, Gln, Glu, Gly, His, Ile, Leu, Met, Phe, Pro, Ser, Thr, Trp, Tyr, or Val, in particular with Pro.

In an embodiment, the variant comprises a substitution at a position corresponding to position 224 with Ala, Arg, Asp, Cys, Gln, Glu, Gly, His, Ile, Leu, Lys, Met, Phe, Pro, Ser, Thr, Trp, Tyr, or Val, in particular with Leu.

In an embodiment, the variant comprises a substitution at a position corresponding to position 242 with Ala, Arg, Asn, Asp, Cys, Gln, Glu, Gly, His, Ile, Leu, Lys, Met, Phe, Pro, Thr, Trp, Tyr, or Val, in particular with Ala, Asp, Glu, Gln, or Met.

In an embodiment, the variant comprises a substitution at a position corresponding to position 254 with Ala, Arg, Asn, Asp, Cys, Glu, Gly, His, Ile, Leu, Lys, Met, Phe, Pro, Ser, Thr, Trp, Tyr, or Val, in particular with Ala, Ser, or Thr.

In an embodiment, the variant comprises a substitution at a position corresponding to position 269 with Ala, Arg, Asn, Cys, Gln, Glu, Gly, His, Ile, Leu, Lys, Met, Phe, Pro, Ser, Thr, Trp, Tyr, or Val, in particular with Gln or Glu.

In an embodiment, the variant comprises a substitution at a position corresponding to position 270 with Ala, Arg, Asn, Asp, Cys, Gln, Glu, Gly, His, Leu, Lys, Met, Phe, Pro, Ser, Thr, Trp, Tyr, or Val, in particular with Leu, Thr, or Val.

In an embodiment, the variant comprises a substitution at a position corresponding to position 274 with Ala, Arg, Asn, Asp, Cys, Gln, Glu, Gly, Ile, Leu, Lys, Met, Phe, Pro, Ser, Thr, Trp, Tyr, or Val, in particular with Arg, Gln, Glu, Lys, or Phe.

In an embodiment, the variant comprises a substitution at a position corresponding to position 276 with Ala, Arg, Asn, Asp, Cys, Gln, Glu, Gly, His, Ile, Leu, Lys, Met, Pro, Ser, Thr, Trp, Tyr, or Val, in particular with Phe.

In an embodiment, the variant comprises a substitution at a position corresponding to position 281 with Ala, Arg, Asn, Cys, Gln, Glu, Gly, His, Ile, Leu, Lys, Met, Phe, Pro, Ser, Thr, Trp, Tyr, or Val, in particular with Asn or Ser.

In an embodiment, the variant comprises a substitution at a position corresponding to position 284 with Ala, Arg, Asn, Asp, Cys, Gln, Glu, Gly, His, Ile, Leu, Lys, Phe, Pro, Ser, Thr, Trp, Tyr, or Val, in particular with His, Thr, or Val.

In an embodiment, the variant comprises a substitution at a position corresponding to position 416 with Ala, Arg, Asn, Asp, Cys, Gln, Glu, His, Ile, Leu, Lys, Met, Phe, Pro, Ser, Thr, Trp, Tyr, or Val, in particular with Ala, Asn, Asp, Ser, Thr, or Val.

In an embodiment, the variant comprises a substitution at a position corresponding to position 427 with Ala, Arg, Asn, Asp, Cys, Gln, Glu, Gly, His, Ile, Lys, Met, Phe, Pro, Ser, Thr, Trp, Tyr, or Val, in particular with Ile, Met, or Val.

In an aspect, the variant comprising a substitution at three positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427. In particular, the variant comprises a substitution at the positions corresponding to positions 129, 177, and 179 or positions 220, 242, and 254.

In another aspect, the variant comprises a substitution at four positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427. In particular, the variant comprises a substitution at the positions corresponding to positions 129, 177, 179, and 208; positions 129, 177, 179, and 242; positions 129, 177, 179, and 284; positions 208, 220, 224, and 254; positions 220, 224, 242, and 254; or positions 220, 224, 254, and 284.

In another aspect, the variant comprises a substitution at five positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427. In particular, the variant comprises a substitution at the positions corresponding to positions 129, 177, 179, 208, and 242; positions 129, 177, 179, 208, and 284; positions 208, 220, 224, 242, and 254; or positions 208, 220, 224, 254, and 284.

In another aspect, the variant comprises a substitution at six positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427. In particular, the variant comprises a substitution at the positions corresponding to positions 129, 177, 179, 208, 242, and 284 or positions 129, 177, 179, 220, 224, and 254.

In another aspect, the variant comprises a substitution at seven positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

In another aspect, the variant comprises a substitution at eight positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

In another aspect, the variant comprises a substitution at nine positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

In another aspect, the variant comprises a substitution at ten positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

The variants preferably have 3-20, e.g., 3-10 and 6-10, alterations such as 3, 4, 5, 6, 7, 8, 9 or 10 alterations. In an embodiment, the alterations are substitutions.

In an embodiment, the variant alpha-amylases comprise or consist of a set of substitutions selected from the group consisting of:

V59A+G108A;
S242Q+M284V;
V59A+M284V;
G108A+M284V;
V59A+G108A+M284V;
V59A+G108A+S242Q+M284V;
E129V+K177L+R179E;
K220P+N224L+Q254S;
E129V+K177L+R179E+M284V;
V59A+E129V+K177L+R179E+H208Y+M284V;
V59A+H208Y+K220P+N224L+Q254S+M284V;
E129V+K177L+R179E+K220P+N224L+Q254S;
V59A+Q89R+E129V+K177L+R179E+H208Y+K220P+ N224L+Q254S;
V59A+E129V+K177L+R179E+H208Y+K220P+ N224L+S242Q+Q254S;
V59A+Q89R+E129V+K177L+R179E+H208Y+K220P+ N224L+Q254S+M284V;
V59A+E129V+K177L+R179E+H208Y+K220P+ N224L+S242Q+Q254S+M284V;
V59A+Q89R+G108A+E129V+K177L+R179E+ H208Y+K220P+N224L+Q254S+M284V; and
V59A+G108A+E129V+K177L+R179E+H208Y+ K220P+N224L+S242Q+Q254S+M284V.

The variants may further comprise a deletion at one or more, e.g., two, three or four, positions corresponding to positions 179, 180, 181 and 182. For example, the variants may comprise a deletion at positions corresponding to positions 181 and 182.

The variants also may further comprise an alteration, preferably a substitution, at a position corresponding to position 193. For example, the alteration at a position corresponding to position 193 may be a substitution with Phe.

The variants also may further comprise a deletion of the amino acid at the position corresponding to positions 376 and/or 377.

In another aspect, the variants further comprise an additional alteration, preferably a substitution, at a position corresponding to position 200, such as a substitution at a position corresponding to position 200 with Leu, Ile, or Thr.

The variants of the present invention preferably consist of 483 to 515, 483 to 493, or 483 to 486 amino acids.

Polynucleotides

The present invention also relates to isolated polynucleotides that encode any of the variants of the present invention.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences.

An isolated polynucleotide encoding a variant may be manipulated in a variety of ways to provide for expression of the variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Darla (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used in the present invention.

Preferred terminators for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos at al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and, when transcribed, is recognized by the host cell as a signal to add polyadenosine residues to transcribed mRNA. Any polyadenylation sequence that is functional in the host cell may be used in the present invention.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that codes for an amino acid sequence linked to the amino terminus of a variant and directs the encoded polypeptide into the cell's secretory pathway. The 5'-end of the coding sequence of the polynucleotide may inherently contain a signal peptide coding region naturally linked in translation reading frame with the segment of the coding region that encodes the secreted variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed polypeptide into the secretory pathway of a host cell may be used in the present invention.

Effective signal peptide coding sequences for bacterial host cells are the signal peptide coding sequences obtained from the genes for *Bacillus* NCIB 11837 maltogenic amylase, *Bacillus licheniformnis* subtilisin, *Bacillus licheniformnis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that codes for an amino acid sequence positioned at the amino terminus of a variant. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences described above may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformnis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of an alpha-amylase variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure alpha-amylase variants.

Host Cells

The present invention also relates to recombinant host cells, comprising a polynucleotide encoding a variant, which are advantageously used in the recombinant production of the variant. A vector comprising a polynucleotide of the present invention is introduced into a host cell so that the vector is maintained as a chromosomal integrant or as a self-replicating extrachromosomal vector as described earlier. The choice of a host cell will to a large extent depend upon the gene encoding the polypeptide and its source.

The host cell may be any cell useful in the recombinant production of a variant, e.g., a prokaryote or a eukaryote.

The prokaryotic host cell may be any gram-positive bacterium or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell, including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-2070, by electroporation (see, e.g., Buckley et al., 1999, Appl. Environ. Microbiol. 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In one aspect, the host cell is a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

In another aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9,* 1980).

In another aspect, the yeast host cell is a *Candida, Hansenula, Kluyveromyces, Pichia, Saccharomyces, Schizosaccharomyces,* or *Yarrowia* cell.

In another aspect, the yeast host cell is a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

In another aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In another aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In another aspect, the filamentous fungal host cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysospodum, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier at al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant from the cultivation medium.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative aspect, the variant is not recovered, but rather a host cell of the present invention expressing a variant is used as a source of the variant.

The variant may be detected using methods known in the art that are specific for the variants. These detection methods may include use of specific antibodies, formation of an enzyme product, or disappearance of an enzyme substrate. For example, an enzyme assay may be used to determine the activity of the polypeptide as described herein in the Examples.

The variant may be recovered by methods known in the art. For example, the polypeptide may be recovered from the nutrient medium by conventional procedures including, but not limited to, collection, centrifugation, filtration, extraction, spray-drying, evaporation, or precipitation.

A variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure variants.

Plants

The present invention also relates to plants, e.g., a transgenic plant, plant part, or plant cell, comprising an isolated polynucleotide encoding a variant of the present invention so as to express and produce the variant in recoverable quantities. The variant may be recovered from the plant or plant part. Alternatively, the plant or plant part containing the recombinant variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a variant of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiol.* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000, the *chlorella* virus adenine methyltransferase gene promoter (Mitra and Higgins, 1994, Plant Mol. Biol. 26: 85-93), or the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having a construct of the present invention to a second plant lacking the construct. For example, a construct encoding a variant or a portion thereof can be introduced into a particular plant variety by crossing, without the need for ever directly transforming a plant of that given variety. Therefore, the present invention not only encompasses a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in a transgene of the present invention being introduced into a plant line by cross pollinating a starting line with a donor plant line that includes a transgene of the present invention. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding a variant of the present invention under conditions conducive for production of the variant; and (b) recovering the variant.

Compositions

The present invention also relates to compositions comprising an alpha-amylase variant and at least one additional enzyme. The additional enzyme(s) may be selected from the group consisting of beta-amylase, cellulase (beta-glucosidase, cellobiohydrolase and endoglucanase), glucoamylase, hemicellulsae (e.g., xylanase), isoamylase, isomerase, lipase, phytase, protease, pullulanase, and/or other enzymes useful in a commercial process in conjunction with an alpha-amylase. The additional enzyme may also be a second alpha-amylase. Such enzymes are known in the art in starch processing, sugar conversion, fermentations for alcohol and other useful end-products, commercial detergents and cleaning aids, stain removal, fabric treatment or desizing, and the like.

Methods of Using the Alpha-Amylase Variants—Industrial Applications

The variants of the present invention possess valuable properties allowing for a variety of industrial applications. In particular, the variants may be used in detergents, in particular laundry detergent compositions and dishwashing detergent compositions, hard surface cleaning compositions, and for desizing textiles, fabrics or garments, production of pulp and paper, beer making, ethanol production, and starch conversion processes.

The alpha-amylase variants may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the variant of the invention also comprise an AMG, pullulanase, and other alpha-amylases.

Further, the variants are particularly useful in the production of sweeteners and ethanol (see, e.g., U.S. Pat. No. 5,231, 017, which is hereby incorporated by reference), such as fuel, drinking and industrial ethanol, from starch or whole grains.

The variants may also be used for desizing of textiles, fabrics, and garments (see, e.g., WO 95/21247, U.S. Pat. No. 4,643,736, and EP 119920, which are incorporated herein by reference), beer making or brewing, and in pulp and paper production or related processes.

Starch Processing

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

In general, alcohol production (ethanol) from whole grain can be separated into 4 main steps: milling, liquefaction, saccharification, and fermentation.

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

In the liquefaction process the starch granules are solubilized by hydrolysis to maltodextrins mostly of a DP higher than 4. The hydrolysis may be carried out by acid treatment or enzymatically by an alpha-amylase. Acid hydrolysis is used on a limited basis. The raw material can be milled whole grain or a side stream from starch processing.

During a typical enzymatic liquefaction, the long-chained starch is degraded into branched and linear shorter units (maltodextrins) by an alpha-amylase. Enzymatic liquefaction is generally carried out as a three-step hot slurry process. The slurry is heated to between 60-95° C. (e.g., 77-86° C., 80-85° C., or 83-85° C.) and the enzyme(s) is (are) added. The liquefaction process is carried out at 85° C. for 1-2 hours. The pH is generally between 5.5 and 6.2. In order to ensure optimal enzyme stability under these conditions, 1 mM of calcium is added (to provide about 40 ppm free calcium ions). After such treatment, the liquefied starch will have a "dextrose equivalent" (DE) of 10-15.

The slurry is subsequently jet-cooked at between 95-140° C., e.g., 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Liquefied starch-containing material is saccharified in the presence of saccharifying enzymes such as glucoamylases. The saccharification process may last for 12 hours to 120 hours (e.g., 12 to 90 hours, 12 to 60 hours and 12 to 48 hours).

However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours.

Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn. Accordingly, in the first aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. In an embodiment a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase variant, or;

(b) saccharifying the liquefied material obtained in step (a) using a carbohydrate-source generating enzyme;

(c) fermenting using a fermenting organism.

In an aspect, a pullulanase such as a family GH57 pullulanase is also used in the liquefaction step. In an embodiment a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In an embodiment the carbohydrate-source generating enzyme is a glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of the genus *Pachykytospora*, e.g., a strain of *Pachykytospora papyracea*; or a strain of the genus *Leucopaxillus*, e.g., *Leucopaxillus giganteus*; or a strain of the genus *Peniophora*, e.g., a strain of the species *Peniophora rufomarginata*; or a mixture thereof. Saccharification step (b) and fermentation step (c) may be carried out either sequentially or simultaneously. A pullulanase and/or metalloprotease may be added during saccharification and/or fermentation when the process is carried out as a sequential saccharification and fermentation process and before or during fermentation when steps (b) and (c) are carried out simultaneously (SSF process). The pullulanase and/or metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Beer Making

The alpha-amylase variants may also be used in a beer-making process and similar fermentations; the alpha-amylases will typically be added during the mashing process. The process is substantially similar to the milling, liquefaction, saccharification, and fermentation processes described above.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pre-treated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch may be further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Pulp and Paper Production

The alpha-amylase variants may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase variants are especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylase variants may also be useful in modifying starch where enzymatically modified starch is used in papermaking together with alkaline fillers such as calcium carbonate, kaolin and clays. With the alpha-amylase variants it is possible to modify the starch in the presence of the filler thus allowing for a simpler integrated process.

Desizing of Textiles, Fabrics and Garments

The alpha-amylase variants may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing process is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size leads to some fiber damage because of the rather aggressive chemicals used. Accordingly, it would be desirable to use the alpha-amylase variants as they have an improved performance in alkaline solutions. The alpha-amylase variants may be used alone or in combination with a cellulase when desizing cellulose-containing fabric or textile.

Desizing and bleaching processes are well known in the art. For instance, such processes are described in e.g., WO 95/21247, U.S. Pat. No. 4,643,736, EP 119920, which are hereby incorporated by reference.

Cleaning Processes and Detergent Compositions

The alpha-amylase variants may be added as a component of a detergent composition for various cleaning or washing processes, including laundry and dishwashing. For example, the variants may be used in the detergent compositions described in WO 96/23874 and WO 97/07202.

The alpha-amylase variants may be incorporated in detergents at conventionally employed concentrations. For example, a variant of the invention may be incorporated in an amount corresponding to 0.00001-10 mg (calculated as pure, active enzyme protein) of alpha-amylase per liter of wash/dishwash liquor using conventional dosing levels of detergent.

The detergent composition may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

The detergent composition may further comprise one or more other enzymes, such as a lipase, peroxidase, protease, another amylolytic enzyme, e.g., another alpha-amylase, glucoamylase, maltogenic amylase, CGTase, cellulase, mannanase (such as Mannaway™ from Novozymes, Denmark)), pectinase, pectin lyase, cutinase, and/or laccase.

In general the properties of the chosen enzyme(s) should be compatible with the selected detergent (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleiclacrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19708 and WO 92/19709.

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The detergent compositions may comprise any enzyme in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

One or more of the variant enzymes described herein may additionally be incorporated in the detergent formulations disclosed in WO 97/07202, which is hereby incorporated as reference.

This disclosure includes further detail in the following examples, which are not in any way intended to limit the scope of what is claimed. The following examples are thus offered to illustrate, but not to limit what is claimed.

EXAMPLES

Assay for Determination of Residual Alpha-Amylase Activity

Residual alpha-amylase activity is determined by a method employing the EnzChek® substrate. The substrate in the EnzChek® Ultra Amylase Assay Kit (E33651, Invitrogen, La Jolla, Calif., USA) is a corn starch derivative, DQ™ starch, which is corn starch labeled with BODIPY® FL dye to such a degree that fluorescence is quenched.

One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (W/v) TRITON® X100, 0.12 mM $CaCl_2$, pH 5.5 is added, vortexed thoroughly and stored at room temperature, in the dark until ready to use. The substrate working solution is prepared by diluting 10-fold in residual activity buffer (100 mM acetate, 0.01% (w/v) TRITON® X100, 0.12 mM CaCl$_2$, pH 5.5) giving a substrate concentration of 100 micrograms/ml. Immediately after incubation the enzyme is diluted to a concentration of 15 ng enzyme protein/mL in 100 mM acetate, 0.01% (W/v) TRITON® X100, 0.12 mM CaCl$_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Glucoamylase Activity (AGU)

A Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 6)) and alpha-amylase variants thereof was determined by incubating the reference alpha-amylase and variants at pH 4.5 and 5.5 and temperatures of 75° C. and 85° C. with 0.12 mM CaCl$_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl$_2$, pH 5.0). Twenty microliters enzyme sample was transferred to 48-well PCR MTP and 180 microliters stability buffer (150 mM acetate, 150 mM MES, 0.01% Triton X100, 0.12 mM CaCl$_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C.

After incubation samples were diluted to 15 ng/ml in residual activity buffer (100 mM Acetate, 0.01% Triton X100, 0.12 mM CaCl$_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½(min)) was calculated using the equation: T½(min)=T(min)*LN(0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference amylase | 21 | 4 | 111 |
| Reference Alpha-Amylase with the substitution V59A | 32 | 6 | 301 |
| Reference Alpha-Amylase with the substitutions V59A + Q89R + E129V + D165N + K177L + R179E + H208Y + K220P + N224L + Q254S | >180 | 29 | ND |
| Reference Alpha-Amylase with the substitutions V59A + Q89R + E129V + W166F + K177L + R179E + H208Y + K220P + N224L + Q254S | >180 | 23 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase with the substitutions V59A + Q89R + E129V + K177L + R179E + H208Y + K220P + N224L + Q254S + M284V | >180 | 49 | ND |
| Reference Alpha-Amylase with the substitutions V59A + E129V + D165N + K177L + R179E + H208Y + K220P + N224L + S242Q + Q254S | >180 | 78 | ND |
| Reference Alpha-Amylase with the substitutions V59A + E129V + E168A + K177L + R179E + H208Y + K220P + N224L + S242Q + Q254S | >180 | 59 | ND |
| Reference Alpha-Amylase with the substitutions V59A + E129V + E168A + K177L + R179E + H208Y + K220P + N224L + Q254S | >180 | 25 | ND |
| Reference Alpha-Amylase with the substitutions V59A + E129V + K171E + K177L + R179E + H208Y + K220P + N224L + S242Q + Q254S | >180 | 72 | ND |
| Reference Alpha-Amylase with the substitutions V59A + E129V + K177L + R179E + A184S + H208Y + K220P + N224L + S242Q + Q254S | >180 | 81 | ND |
| Reference Alpha-Amylase with the substitutions V59A + E129V + K177L + R179E + H208Y + K220P + N224L + S242Q + Q254S + M284V | >180 | 141 | ND |
| Reference Alpha-Amylase with the substitution V59E | 28 | 5 | 230 |
| Reference Alpha-Amylase with the substitution V59I | 28 | 5 | 210 |
| Reference Alpha-Amylase with the substitution V59Q | 30 | 6 | 250 |
| Reference Alpha-Amylase with the substitution G108A | 41 | 7.1 | 286 |
| Reference Alpha-Amylase with the substitutions V59A + Q89R + G112D + E129V + K177L + R179E + K220P + N224L + Q254S | 149 | 22 | ND |
| Reference Alpha-Amylase with the substitutions V59A + Q89R + E129V + K177L + R179E + H208Y + K220P + N224L + Q254S | >180 | 28 | ND |
| Reference Alpha-Amylase with the substitutions V59A + Q89R + E129V + K177L + R179E + K220P + N224L + Q254S + D269E + D281N | 112 | 16 | ND |
| Reference Alpha-Amylase with the substitutions V59A + Q89R + E129V + K177L + R179E + K220P + N224L + Q254S + I270L | 168 | 21 | ND |
| Reference Alpha-Amylase with the substitutions V59A + Q89R + E129V + K177L + R179E + K220P + N224L + Q254S + H274K | >180 | 24 | ND |
| Reference Alpha-Amylase with the substitutions V59A + Q89R + E129V + K177L + R179E + K220P + N224L + Q254S + Y276F | 91 | 15 | ND |
| Reference Alpha-Amylase with the substitutions V59A + E129V + R157Y + K177L + R179E + K220P + N224L + S242Q + Q254S | 141 | 41 | ND |
| Reference Alpha-Amylase with the substitutions V59A + E129V + K177L + R179E + H208Y + K220P + N224L + S242Q + Q254S | >180 | 62 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase with the substitutions V59A + E129V + K177L + R179E + K220P + N224L + S242Q + Q254S | >180 | 49 | >480 |
| Reference Alpha-Amylase with the substitutions V59A + E129V + K177L + R179E + K220P + N224L + S242Q + Q254S + H274K | >180 | 53 | ND |
| Reference Alpha-Amylase with the substitutions V59A + E129V + K177L + R179E + K220P + N224L + S242Q + Q254S + Y276F | >180 | 57 | ND |
| Reference Alpha-Amylase with the substitutions V59A + E129V + K177L + R179E + K220P + N224L + S242Q + Q254S + D281N | >180 | 37 | ND |
| Reference Alpha-Amylase with the substitutions V59A + E129V + K177L + R179E + K220P + N224L + S242Q + Q254S + M284T | >180 | 51 | ND |
| Reference Alpha-Amylase with the substitutions V59A + E129V + K177L + R179E + K220P + N224L + S242Q + Q254S + G416V | >180 | 45 | ND |
| Reference Alpha-Amylase with the substitutions V59A + E129V + K177L + R179E + K220P + N224L + Q254S | 143 | 21 | >480 |
| Reference Alpha-Amylase with the substitutions V59A + E129V + K177L + R179E + K220P + N224L + Q254S + M284T | >180 | 22 | ND |
| Reference Alpha-Amylase with the substitutions A91L + M96I + E129V + K177L + R179E + K220P + N224L + S242Q + Q254S | >180 | 38 | ND |
| Reference Alpha-Amylase with the substitutions E129V + K177L + R179E | 57 | 11 | 402 |
| Reference Alpha-Amylase with the substitutions E129V + K177L + R179E + K220P + N224L + S242Q + Q254S | 174 | 44 | >480 |
| Reference Alpha-Amylase with the substitutions E129V + K177L + R179E + K220P + N224L + S242Q + Q254S + Y276F + L427M | >180 | 49 | >480 |
| Reference Alpha-Amylase with the substitutions E129V + K177L + R179E + K220P + N224L + S242Q + Q254S + M284T | >180 | 49 | >480 |
| Reference Alpha-Amylase with the substitutions E129V + K177L + R179E + K220P + N224L + S242Q + Q254S + N376* + I377* | 177 | 36 | >480 |
| Reference Alpha-Amylase with the substitutions E129V + K177L + R179E + K220P + N224L + Q254S | 94 | 13 | >480 |
| Reference Alpha-Amylase with the substitutions E129V + K177L + R179E + K220P + N224L + Q254S + M284T | 129 | 24 | >480 |
| Reference Alpha-Amylase with the substitutions E129V + K177L + R179E + S242Q | 148 | 30 | >480 |
| Reference Alpha-Amylase with the substitutions E129V + K177L + R179V | 78 | 9 | >480 |
| Reference Alpha-Amylase with the substitutions E129V + K177L + R179V + K220P + N224L + S242Q + Q254S | 178 | 31 | >480 |
| Reference Alpha-Amylase with the substitutions K220P + N224L + S242Q + Q254S | 66 | 17 | >480 |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase with the substitutions K220P + N224L + Q254S | 30 | 6 | 159 |
| Reference Alpha-Amylase with the substitution M284T | 35 | 7 | 278 |
| Reference Alpha-Amylase with the substitutions M284V | 59 | 13 | ND |

ND not determined

The results demonstrate that the alpha-amylase variants have a significantly greater half-life and stability than the reference alpha-amylase.

Example 2

Production of Ethanol Using Alpha-Amylase Variants

Four small scale mashes of the reference alpha-amylase and two alpha-amylase variants described in Example 1 were prepared as follows: about 54 g corn ground, about 51 g tap water, and about 45 g backset were mixed in a 250 mL plastic bottle to a total slurry weight of 150 g. The pH of the corn slurry was adjusted to 4.5. The enzymes were added to the mashes at 2 micrograms of amylase per gram of dry solids. For liquefaction, the alpha-amylases were added to the bottles and the bottles were mixed thoroughly and placed into a preheated 85° C. water bath. The samples were held in the water bath for 2 hours at pH 4.5 while being shaken every 10 minutes for the first 30 minutes and every 30 minutes thereafter for the remainder of the 2 hour liquefaction. The samples were then cooled in an ice bath; pH was adjusted to 5.0, and 0.75 mL urea and 0.45 mL penicillin were added to reach final concentrations of 1000 and 3 ppm in the mashes, respectively. The samples were then subjected to simultaneous saccharification and fermentation (SSF) with Sprizyme Fuel (a glucoamylase product sold by Novozymes).

Five gram aliquots of the mashes were transferred into pre-weighed conical centrifuge tubes, using 5 replicates per mash. SSF was then performed on these mashes in a 32° C. water bath for 54 hours using Sprizyme Fuel as the glucoamylase. The glucoamylase dose was 0.50 AGU/g DS for all fermentations. The CO$_2$ weight loss during SSF was measured and ethanol was quantified using HPLC after 54 hours of SSF. The average 54 hour HPLC SSF data are provided in Table 2 below.

TABLE 2

Ethanol Yields After 54 Hours Fermentation

| Alpha-Amylase | Ethanol, g/L | Std dev. |
|---|---|---|
| Reference Alpha-Amylase | 105.5946 | 0.3708 |
| Reference Alpha-Amylase with the substitutions E129V + K177L + R179E | 119.4197 | 0.8927 |
| Reference Alpha-Amylase with the substitutions K220P + N224L + Q254S | 116.4867 | 0.5922 |

The results demonstrate that the use of the alpha-amylase variants resulted in a significantly greater yield of ethanol relative to the reference alpha-amylase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention is further defined by the following paragraphs:

Paragraph 1. An isolated variant alpha-amylase, comprising a substitution at three or more (several) positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, wherein the variant has at least 65% and less than 100% sequence identity with the mature polypeptide of SEQ ID NO: 1, 2, 3, 4, 5, 6, and/or 7 and the variant has alpha-amylase activity.

Paragraph 2. The variant of paragraph 1, which comprises a substitution at a position corresponding to position 59 with Ala, Arg, Asn, Asp, Cys, Gln, Glu, Gly, His, Ile, Leu, Lys, Met, Phe, Pro, Ser, Thr, Trp, or Tyr, in particular with Ala, Gln, Glu, Gly, Ile, Leu, Pro, or Thr.

Paragraph 3. The variant of paragraph 1 or 2, which comprises a substitution at a position corresponding to position 89 with Ala, Arg, Asn, Asp, Cys, Glu, Gly, His, Ile, Leu, Lys, Met, Phe, Pro, Ser, Thr, Trp, Tyr, or Val, in particular with Arg, His, or Lys.

Paragraph 4. The variant of any of paragraphs 1-3, which comprises a substitution at a position corresponding to position 91 with Arg, Asn, Asp, Cys, Gln, Glu, Gly, His, Ile, Leu, Lys, Met, Phe, Pro, Ser, Thr, Trp, Tyr, or Val, in particular with Ile, Leu, or Val.

Paragraph 5. The variant of any of paragraphs 1-4, which comprises a substitution at a position corresponding to position 96 with Ala, Arg, Asn, Asp, Cys, Gln, Glu, Gly, His, Ile, Leu, Lys, Phe, Pro, Ser, Thr, Trp, Tyr, or Val, in particular with Ile, Leu, or Val.

Paragraph 6. The variant of any of paragraphs 1-5, which comprises a substitution at a position corresponding to position 108 with Ala, Arg, Asn, Asp, Cys, Gln, Glu, His, Ile, Leu, Lys, Met, Phe, Pro, Ser, Thr, Trp, Tyr, or Val, in particular with Ala.

Paragraph 7. The variant of any of paragraphs 1-6, which comprises a substitution at a position corresponding to position 112 with Ala, Arg, Asn, Asp, Cys, Gln, Glu, His, Ile, Leu, Lys, Met, Phe, Pro, Ser, Thr, Trp, Tyr, or Val, in particular with Ala, Asp, or Glu.

Paragraph 8. The variant of any of paragraphs 1-7, which comprises a substitution at a position corresponding to position 129 with Ala, Arg, Asn, Asp, Cys, Gln, Gly, His, Ile, Leu, Lys, Met, Phe, Pro, Ser, Thr, Trp, Tyr, or Val, in particular with Ala, Thr, or Val.

Paragraph 9. The variant of any of paragraphs 1-8, which comprises a substitution at a position corresponding to position 157 with Ala, Asn, Asp, Cys, Gln, Glu, Gly, His, Ile, Leu, Lys, Met, Phe, Pro, Ser, Thr, Trp, Tyr, or Val, in particular with His, Lys, Phe, or Tyr.

Paragraph 10. The variant of any of paragraphs 1-9, which comprises a substitution at a position corresponding to position 165 Ala, Arg, Asn, Cys, Gln, Glu, Gly, His, Ile, Leu, Lys, Met, Phe, Pro, Ser, Thr, Trp, Tyr, or Val, in particular with Asn.

Paragraph 11. The variant of any of paragraphs 1-10, which comprises a substitution at a position corresponding to position 166 Ala, Arg, Asn, Asp, Cys, Gln, Glu, Gly, His, Ile, Leu, Lys, Met, Phe, Pro, Ser, Thr, Tyr, or Val, in particular with Phe.

Paragraph 12. The variant of any of paragraphs 1-11, which comprises a substitution at a position corresponding to position 168 with Ala, Arg, Asn, Asp, Cys, Gln, Gly, His, Ile, Leu, Lys, Met, Phe, Pro, Ser, Thr, Trp, Tyr, or Val, in particular with Ala.

Paragraph 13. The variant of any of paragraphs 1-12, which comprises a substitution at a position corresponding to position 171 with Ala, Arg, Asn, Asp, Cys, Gln, Glu, Gly, His, Ile, Leu, Met, Phe, Pro, Ser, Thr, Trp, Tyr, or Val, in particular with Glu.

Paragraph 14. The variant of any of paragraphs 1-13, which comprises a substitution at a position corresponding to position 177 with Ala, Arg, Asn, Asp, Cys, Gln, Glu, Gly, His, Ile, Leu, Met, Phe, Pro, Ser, Thr, Trp, Tyr, or Val, in particular with Arg, Leu, or Met.

Paragraph 15. The variant of any of paragraphs 1-14, which comprises a substitution at a position corresponding to position 179 with Ala, Asn, Asp, Cys, Gln, Glu, Gly, His, Ile, Leu, Lys, Met, Phe, Pro, Ser, Thr, Trp, Tyr, or Val, in particular with Gln, Glu, Ile, Leu, Lys, or Val.

Paragraph 16. The variant of any of paragraphs 1-15, which comprises a substitution at a position corresponding to position 180 with Ala, Arg, Asn, Asp, Cys, Gln, Glu, His, Ile, Leu, Lys, Met, Phe, Pro, Ser, Thr, Trp, Tyr, or Val, in particular with Glu or Val.

Paragraph 17. The variant of any of paragraphs 1-16, which comprises a substitution at a position corresponding to position 181 with Ala, Arg, Asn, Asp, Cys, Gln, Glu, Gly, His, Leu, Lys, Met, Phe, Pro, Ser, Thr, Trp, Tyr, or Val, in particular with Glu, Gly, or Val.

Paragraph 18. The variant of any of paragraphs 1-17, which comprises a substitution at a position corresponding to position 184 with Arg, Asn, Asp, Cys, Gln, Glu, Gly, His, Ile, Leu, Lys, Met, Phe, Pro, Ser, Thr, Trp, Tyr, or Val, in particular with Ser.

Paragraph 19. The variant of any of paragraphs 1-18, which comprises a substitution at a position corresponding to position 208 with Ala, Arg, Asn, Asp, Cys, Gln, Glu, Gly, Ile, Leu, Lys, Met, Phe, Pro, Ser, Thr, Trp, Tyr, or Val, in particular with Phe or Tyr.

Paragraph 20. The variant of any of paragraphs 1-19, which comprises a substitution at a position corresponding to position 220 with Ala, Arg, Asn, Asp, Cys, Gln, Glu, Gly, His, Ile, Leu, Met, Phe, Pro, Ser, Thr, Trp, Tyr, or Val, in particular with Pro.

Paragraph 21. The variant of any of paragraphs 1-20, which comprises a substitution at a position corresponding to position 224 with Ala, Arg, Asp, Cys, Gln, Glu, Gly, His, Ile, Leu, Lys, Met, Phe, Pro, Ser, Thr, Trp, Tyr, or Val, in particular with Leu.

Paragraph 22. The variant of any of paragraphs 1-21, which comprises a substitution at a position corresponding to position 242 with Ala, Arg, Asn, Asp, Cys, Gln, Glu, Gly, His, Ile, Leu, Lys, Met, Phe, Pro, Thr, Trp, Tyr, or Val, in particular with Ala, Asp, Glu, Gln, or Met.

Paragraph 23. The variant of any of paragraphs 1-22, which comprises a substitution at a position corresponding to position 254 with Ala, Arg, Asn, Asp, Cys, Glu, Gly, His, Ile, Leu, Lys, Met, Phe, Pro, Ser, Thr, Trp, Tyr, or Val, in particular with Ala, Ser, or Thr.

Paragraph 24. The variant of any of paragraphs 1-23, which comprises a substitution at a position corresponding to position 269 with Ala, Arg, Asn, Cys, Gln, Glu, Gly, His, Ile, Leu, Lys, Met, Phe, Pro, Ser, Thr, Trp, Tyr, or Val, in particular with Gln or Glu.

Paragraph 25. The variant of any of paragraphs 1-24, which comprises a substitution at a position corresponding to position 270 with Ala, Arg, Asn, Asp, Cys, Gln, Glu, Gly, His, Leu, Lys, Met, Phe, Pro, Ser, Thr, Trp, Tyr, or Val, in particular with Leu, Thr, or Val.

Paragraph 26. The variant of any of paragraphs 1-25, which comprises a substitution at a position corresponding to position 274 with Ala, Arg, Asn, Asp, Cys, Gln, Glu, Gly, Ile, Leu, Lys, Met, Phe, Pro, Ser, Thr, Trp, Tyr, or Val, in particular with Arg, Gln, Glu, Lys, or Phe.

Paragraph 27. The variant of any of paragraphs 1-26, which comprises a substitution at a position corresponding to position 276 with Ala, Arg, Asn, Asp, Cys, Gln, Glu, Gly, His, Ile, Leu, Lys, Met, Phe, Pro, Ser, Thr, Trp, or Val, in particular with Phe.

Paragraph 28. The variant of any of paragraphs 1-27, which comprises a substitution at a position corresponding to position 281 with Ala, Arg, Asn, Cys, Gln, Glu, Gly, His, Ile, Leu, Lys, Met, Phe, Pro, Ser, Thr, Trp, Tyr, or Val, in particular with Asn or Ser.

Paragraph 29. The variant of any of paragraphs 1-28, which comprises a substitution at a position corresponding to position 284 with Ala, Arg, Asn, Asp, Cys, Gln, Glu, Gly, His, Ile, Leu, Lys, Phe, Pro, Ser, Thr, Trp, Tyr, or Val, in particular with His, Thr, or Val.

Paragraph 30. The variant of any of paragraphs 1-29, which comprises a substitution at a position corresponding to position 416 with Ala, Arg, Asn, Asp, Cys, Gln, Glu, His, Ile, Leu, Lys, Met, Phe, Pro, Ser, Thr, Trp, Tyr, or Val, in particular with Ala, Asn, Asp, Ser, Thr, or Val.

Paragraph 31. The variant of any of paragraphs 1-30, which comprises a substitution at a position corresponding to position 427 with Ala, Arg, Asn, Asp, Cys, Gln, Glu, Gly, His, Ile, Lys, Met, Phe, Pro, Ser, Thr, Trp, Tyr, or Val, in particular with Ile, Met, or Val.

Paragraph 32. The variant of any of paragraphs 1-31, comprising a substitution at three positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, in particular, at the positions corresponding to positions 129, 177, and 179 or positions 220, 242, and 254.

Paragraph 33. The variant of paragraph 32, wherein the three positions are selected from the group consisting of:
Positions 59, 89, and 129;
Positions 59, 89, and 177;
Positions 59, 89, and 179;
Positions 59, 89, and 180;
Positions 59, 89, and 181;
Positions 59, 89, and 220;
Positions 59, 89, and 224;
Positions 59, 89, and 242;

Positions 59, 89, and 254;
Positions 59, 108, and 284;
Positions 59, 129, and 177;
Positions 59, 129, and 179;
Positions 59, 129, and 180;
Positions 59, 129, and 181;
Positions 59, 129, and 220;
Positions 59, 129, and 224;
Positions 59, 129, and 242;
Positions 59, 129, and 254;
Positions 59, 177, and 179;
Positions 59, 177, and 180;
Positions 59, 177, and 181;
Positions 59, 177, and 220;
Positions 59, 177, and 224;
Positions 59, 177, and 242;
Positions 59, 177, and 254;
Positions 59, 179, and 181;
Positions 59, 179, and 220;
Positions 59, 179, and 224;
Positions 59, 179, and 242;
Positions 59, 179, and 254;
Positions 59, 180, and 181;
Positions 59, 180, and 220;
Positions 59, 180, and 224;
Positions 59, 180, and 242;
Positions 59, 180, and 254;
Positions 59, 181, and 220;
Positions 59, 181, and 224;
Positions 59, 181, and 242;
Positions 59, 181, and 254;
Positions 59, 220, and 224;
Positions 59, 220, and 242;
Positions 59, 220, and 254;
Positions 59, 224, and 242;
Positions 59, 224, and 254;
Positions 59, 242, and 254;
Positions 89, 129, and 177;
Positions 89, 129, and 179;
Positions 89, 129, and 180;
Positions 89, 129, and 181;
Positions 89, 129, and 220;
Positions 89, 129, and 224;
Positions 89, 129, and 242;
Positions 89, 129, and 254;
Positions 89, 177, and 179;
Positions 89, 177, and 180;
Positions 89, 177, and 181;
Positions 89, 177, and 220;
Positions 89, 177, and 224;
Positions 89, 177, and 242;
Positions 89, 177, and 254;
Positions 89, 179, and 181;
Positions 89, 179, and 220;
Positions 89, 179, and 224;
Positions 89, 179, and 242;
Positions 89, 179, and 254;
Positions 89, 180, and 181;
Positions 89, 180, and 220;
Positions 89, 180, and 224;
Positions 89, 180, and 242;
Positions 89, 180, and 254;
Positions 89, 181, and 220;
Positions 89, 181, and 224;
Positions 89, 181, and 242;
Positions 89, 181, and 254;
Positions 89, 220, and 224;
Positions 89, 220, and 242;
Positions 89, 220, and 254;
Positions 89, 224, and 242;
Positions 89, 224, and 254;
Positions 89, 242, and 254;
Positions 129, 177, and 179;
Positions 129, 177, and 180;
Positions 129, 177, and 181;
Positions 129, 177, and 220;
Positions 129, 177, and 224;
Positions 129, 177, and 242;
Positions 129, 177, and 254;
Positions 129, 179, and 181;
Positions 129, 179, and 220;
Positions 129, 179, and 224;
Positions 129, 179, and 242;
Positions 129, 179, and 254;
Positions 129, 180, and 181;
Positions 129, 180, and 220;
Positions 129, 180, and 224;
Positions 129, 180, and 242;
Positions 129, 180, and 254;
Positions 129, 181, and 220;
Positions 129, 181, and 224;
Positions 129, 181, and 242;
Positions 129, 181, and 254;
Positions 129, 220, and 224;
Positions 129, 220, and 242;
Positions 129, 220, and 254;
Positions 129, 224, and 242;
Positions 129, 224, and 254;
Positions 129, 242, and 254;
Positions 177, 179, and 181;
Positions 177, 179, and 220;
Positions 177, 179, and 224;
Positions 177, 179, and 242;
Positions 177, 179, and 254;
Positions 177, 180, and 181;
Positions 177, 180, and 220;
Positions 177, 180, and 224;
Positions 177, 180, and 242;
Positions 177, 180, and 254;
Positions 177, 181, and 220;
Positions 177, 181, and 224;
Positions 177, 181, and 242;
Positions 177, 181, and 254;
Positions 177, 220, and 224;
Positions 177, 220, and 242;
Positions 177, 220, and 254;
Positions 177, 224, and 242;
Positions 177, 224, and 254;
Positions 177, 242, and 254;
Positions 179, 181, and 220;
Positions 179, 181, and 224;
Positions 179, 181, and 242;
Positions 179, 181, and 254;
Positions 179, 220, and 224;
Positions 179, 220, and 242;
Positions 179, 220, and 254;
Positions 179, 224, and 242;
Positions 179, 224, and 254;
Positions 179, 242, and 254;
Positions 180, 181, and 220;
Positions 180, 181, and 224;
Positions 180, 181, and 242;
Positions 180, 181, and 254;
Positions 180, 220, and 224;

Positions 180, 220, and 242;
Positions 180, 220, and 254;
Positions 180, 224, and 242;
Positions 180, 224, and 254;
Positions 180, 242, and 254;
Positions 181, 220, and 224;
Positions 181, 220, and 242;
Positions 181, 220, and 254;
Positions 181, 224, and 242;
Positions 181, 224, and 254;
Positions 181, 242, and 254;
Positions 220, 224, and 242;
Positions 220, 224, and 254; and
Positions 224, 242, and 254.

Paragraph 34. The variant of any of paragraphs 1-31, comprising a substitution at four positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, in particular, at the positions corresponding to positions 129, 177, 179, and 208; positions 129, 177, 179, and 242; positions 129, 177, 179, and 284; positions 208, 220, 224, and 254; positions 220, 224, 242, and 254; or positions 220, 224, 254, and 284.

Paragraph 35. The variant of paragraph 34, wherein the four positions are selected from the group consisting of:
Positions 59, 89, 129, and 177;
Positions 59, 89, 129, and 179;
Positions 59, 89, 129, and 180;
Positions 59, 89, 129, and 181;
Positions 59, 89, 129, and 220;
Positions 59, 89, 129, and 224;
Positions 59, 89, 129, and 242;
Positions 59, 89, 129, and 254;
Positions 59, 89, 177, and 179;
Positions 59, 89, 177, and 180;
Positions 59, 89, 177, and 181;
Positions 59, 89, 177, and 220;
Positions 59, 89, 177, and 224;
Positions 59, 89, 177, and 242;
Positions 59, 89, 177, and 254;
Positions 59, 89, 179, and 181;
Positions 59, 89, 179, and 220;
Positions 59, 89, 179, and 224;
Positions 59, 89, 179, and 242;
Positions 59, 89, 179, and 254;
Positions 59, 89, 180, and 181;
Positions 59, 89, 180, and 220;
Positions 59, 89, 180, and 224;
Positions 59, 89, 180, and 242;
Positions 59, 89, 180, and 254;
Positions 59, 89, 181, and 220;
Positions 59, 89, 181, and 224;
Positions 59, 89, 181, and 242;
Positions 59, 89, 181, and 254;
Positions 59, 89, 220, and 224;
Positions 59, 89, 220, and 242;
Positions 59, 89, 220, and 254;
Positions 59, 89, 224, and 242;
Positions 59, 89, 224, and 254;
Positions 59, 89, 242, and 254;
Positions 59, 108, 242, and 284;
Positions 59, 129, 177, and 179;
Positions 59, 129, 177, and 180;
Positions 59, 129, 177, and 181;
Positions 59, 129, 177, and 220;
Positions 59, 129, 177, and 224;
Positions 59, 129, 177, and 242;
Positions 59, 129, 177, and 254;
Positions 59, 129, 179, and 181;
Positions 59, 129, 179, and 220;
Positions 59, 129, 179, and 224;
Positions 59, 129, 179, and 242;
Positions 59, 129, 179, and 254;
Positions 59, 129, 180, and 181;
Positions 59, 129, 180, and 220;
Positions 59, 129, 180, and 224;
Positions 59, 129, 180, and 242;
Positions 59, 129, 180, and 254;
Positions 59, 129, 181, and 220;
Positions 59, 129, 181, and 224;
Positions 59, 129, 181, and 242;
Positions 59, 129, 181, and 254;
Positions 59, 129, 220, and 224;
Positions 59, 129, 220, and 242;
Positions 59, 129, 220, and 254;
Positions 59, 129, 224, and 242;
Positions 59, 129, 224, and 254;
Positions 59, 129, 242, and 254;
Positions 59, 177, 179, and 181;
Positions 59, 177, 179, and 220;
Positions 59, 177, 179, and 224;
Positions 59, 177, 179, and 242;
Positions 59, 177, 179, and 254;
Positions 59, 177, 180, and 181;
Positions 59, 177, 180, and 220;
Positions 59, 177, 180, and 224;
Positions 59, 177, 180, and 242;
Positions 59, 177, 180, and 254;
Positions 59, 177, 181, and 220;
Positions 59, 177, 181, and 224;
Positions 59, 177, 181, and 242;
Positions 59, 177, 181, and 254;
Positions 59, 177, 220, and 224;
Positions 59, 177, 220, and 242;
Positions 59, 177, 220, and 254;
Positions 59, 177, 224, and 242;
Positions 59, 177, 224, and 254;
Positions 59, 177, 242, and 254;
Positions 59, 179, 181, and 220;
Positions 59, 179, 181, and 224;
Positions 59, 179, 181, and 242;
Positions 59, 179, 181, and 254;
Positions 59, 179, 220, and 224;
Positions 59, 179, 220, and 242;
Positions 59, 179, 220, and 254;
Positions 59, 179, 224, and 242;
Positions 59, 179, 224, and 254;
Positions 59, 179, 242, and 254;
Positions 59, 180, 181, and 220;
Positions 59, 180, 181, and 224;
Positions 59, 180, 181, and 242;
Positions 59, 180, 181, and 254;
Positions 59, 180, 220, and 224;
Positions 59, 180, 220, and 242;
Positions 59, 180, 220, and 254;
Positions 59, 180, 224, and 242;
Positions 59, 180, 224, and 254;
Positions 59, 180, 242, and 254;
Positions 59, 181, 220, and 224;
Positions 59, 181, 220, and 242;
Positions 59, 181, 220, and 254;
Positions 59, 181, 224, and 242;
Positions 59, 181, 224, and 254;
Positions 59, 181, 242, and 254;

Positions 59, 220, 224, and 242;
Positions 59, 220, 224, and 254;
Positions 59, 220, 242, and 254;
Positions 59, 224, 242, and 254;
Positions 89, 129, 177, and 179;
Positions 89, 129, 177, and 180;
Positions 89, 129, 177, and 181;
Positions 89, 129, 177, and 220;
Positions 89, 129, 177, and 224;
Positions 89, 129, 177, and 242;
Positions 89, 129, 177, and 254;
Positions 89, 129, 179, and 181;
Positions 89, 129, 179, and 220;
Positions 89, 129, 179, and 224;
Positions 89, 129, 179, and 242;
Positions 89, 129, 179, and 254;
Positions 89, 129, 180, and 181;
Positions 89, 129, 180, and 220;
Positions 89, 129, 180, and 224;
Positions 89, 129, 180, and 242;
Positions 89, 129, 180, and 254;
Positions 89, 129, 181, and 220;
Positions 89, 129, 181, and 224;
Positions 89, 129, 181, and 242;
Positions 89, 129, 181, and 254;
Positions 89, 129, 220, and 224;
Positions 89, 129, 220, and 242;
Positions 89, 129, 220, and 254;
Positions 89, 129, 224, and 242;
Positions 89, 129, 224, and 254;
Positions 89, 129, 242, and 254;
Positions 89, 177, 179, and 181;
Positions 89, 177, 179, and 220;
Positions 89, 177, 179, and 224;
Positions 89, 177, 179, and 242;
Positions 89, 177, 179, and 254;
Positions 89, 177, 180, and 181;
Positions 89, 177, 180, and 220;
Positions 89, 177, 180, and 224;
Positions 89, 177, 180, and 242;
Positions 89, 177, 180, and 254;
Positions 89, 177, 181, and 220;
Positions 89, 177, 181, and 224;
Positions 89, 177, 181, and 242;
Positions 89, 177, 181, and 254;
Positions 89, 179, 181, and 220;
Positions 89, 179, 181, and 224;
Positions 89, 179, 181, and 242;
Positions 89, 179, 181, and 254;
Positions 89, 179, 220, and 224;
Positions 89, 179, 220, and 242;
Positions 89, 179, 220, and 254;
Positions 89, 179, 224, and 242;
Positions 89, 179, 224, and 254;
Positions 89, 179, 242, and 254;
Positions 89, 180, 181, and 220;
Positions 89, 180, 181, and 224;
Positions 89, 180, 181, and 242;
Positions 89, 180, 181, and 254;
Positions 89, 180, 220, and 224;
Positions 89, 180, 220, and 242;
Positions 89, 180, 220, and 254;
Positions 89, 180, 224, and 242;
Positions 89, 180, 224, and 254;
Positions 89, 180, 242, and 254;
Positions 89, 181, 220, and 224;
Positions 89, 181, 220, and 242;
Positions 89, 181, 220, and 254;
Positions 89, 181, 224, and 242;
Positions 89, 181, 224, and 254;
Positions 89, 181, 242, and 254;
Positions 89, 220, 224, and 242;
Positions 89, 220, 224, and 254;
Positions 89, 220, 242, and 254;
Positions 89, 224, 242, and 254;
Positions 129, 177, 179, and 181;
Positions 129, 177, 179, and 220;
Positions 129, 177, 179, and 224;
Positions 129, 177, 179, and 242;
Positions 129, 177, 179, and 254;
Positions 129, 177, 179, and 284;
Positions 129, 177, 180, and 181;
Positions 129, 177, 180, and 220;
Positions 129, 177, 180, and 224;
Positions 129, 177, 180, and 242;
Positions 129, 177, 180, and 254;
Positions 129, 177, 181, and 220;
Positions 129, 177, 181, and 224;
Positions 129, 177, 181, and 242;
Positions 129, 177, 181, and 254;
Positions 129, 177, 220, and 224;
Positions 129, 177, 220, and 242;
Positions 129, 177, 220, and 254;
Positions 129, 177, 224, and 242;
Positions 129, 177, 224, and 254;
Positions 129, 177, 242, and 254;
Positions 129, 179, 181, and 220;
Positions 129, 179, 181, and 224;
Positions 129, 179, 181, and 242;
Positions 129, 179, 181, and 254;
Positions 129, 179, 220, and 224;
Positions 129, 179, 220, and 242;
Positions 129, 179, 220, and 254;
Positions 129, 179, 224, and 242;
Positions 129, 179, 224, and 254;
Positions 129, 179, 242, and 254;
Positions 129, 180, 181, and 220;
Positions 129, 180, 181, and 224;
Positions 129, 180, 181, and 242;
Positions 129, 180, 181, and 254;
Positions 129, 180, 220, and 224;
Positions 129, 180, 220, and 242;
Positions 129, 180, 220, and 254;
Positions 129, 180, 224, and 242;
Positions 129, 180, 224, and 254;
Positions 129, 180, 242, and 254;
Positions 129, 181, 220, and 224;
Positions 129, 181, 220, and 242;
Positions 129, 181, 220, and 254;
Positions 129, 181, 224, and 242;
Positions 129, 181, 224, and 254;
Positions 129, 181, 242, and 254;
Positions 129, 220, 224, and 242;
Positions 129, 220, 224, and 254;
Positions 129, 220, 242, and 254;
Positions 129, 224, 242, and 254;
Positions 177, 179, 181, and 220;
Positions 177, 179, 181, and 224;
Positions 177, 179, 181, and 242;
Positions 177, 179, 181, and 254;
Positions 177, 179, 220, and 224;
Positions 177, 179, 220, and 242;
Positions 177, 179, 220, and 254;
Positions 177, 179, 224, and 242;

Positions 177, 179, 224, and 254;
Positions 177, 179, 242, and 254;
Positions 177, 180, 181, and 220;
Positions 177, 180, 181, and 224;
Positions 177, 180, 181, and 242;
Positions 177, 180, 181, and 254;
Positions 177, 180, 220, and 224;
Positions 177, 180, 220, and 242;
Positions 177, 180, 220, and 254;
Positions 177, 180, 224, and 242;
Positions 177, 180, 224, and 254;
Positions 177, 180, 242, and 254;
Positions 177, 181, 220, and 224;
Positions 177, 181, 220, and 242;
Positions 177, 181, 220, and 254;
Positions 177, 181, 224, and 242;
Positions 177, 181, 224, and 254;
Positions 177, 181, 242, and 254;
Positions 177, 220, 224, and 242;
Positions 177, 220, 224, and 254;
Positions 177, 220, 242, and 254;
Positions 177, 224, 242, and 254;
Positions 179, 181, 220, and 224;
Positions 179, 181, 220, and 242;
Positions 179, 181, 220, and 254;
Positions 179, 181, 224, and 242;
Positions 179, 181, 224, and 254;
Positions 179, 181, 242, and 254;
Positions 179, 220, 224, and 242;
Positions 179, 220, 224, and 254;
Positions 179, 220, 242, and 254;
Positions 179, 224, 242, and 254;
Positions 180, 181, 220, and 224;
Positions 180, 181, 220, and 242;
Positions 180, 181, 220, and 254;
Positions 180, 181, 224, and 242;
Positions 180, 181, 224, and 254;
Positions 180, 181, 242, and 254;
Positions 180, 220, 224, and 242;
Positions 180, 220, 224, and 254;
Positions 180, 220, 242, and 254;
Positions 180, 224, 242, and 254;
Positions 181, 220, 224, and 242;
Positions 181, 220, 224, and 254;
Positions 181, 220, 242, and 254;
Positions 181, 224, 242, and 254; and
Positions 220, 224, 242, and 254.

Paragraph 36. The variant of any of paragraphs 1-31, comprising a substitution at five positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, in particular, at the positions corresponding to positions 129, 177, 179, 208, and 242; positions 129, 177, 179, 208, and 284; positions 208, 220, 224, 242, and 254; or positions 208, 220, 224, 254, and 284.

Paragraph 37. The variant of paragraph 36, wherein the five positions are selected from the group consisting of:
Positions 59, 89, 129, 177, and 179;
Positions 59, 89, 129, 177, and 180;
Positions 59, 89, 129, 177, and 181;
Positions 59, 89, 129, 177, and 220;
Positions 59, 89, 129, 177, and 224;
Positions 59, 89, 129, 177, and 242;
Positions 59, 89, 129, 177, and 254;
Positions 59, 89, 129, 179, and 181;
Positions 59, 89, 129, 179, and 220;
Positions 59, 89, 129, 179, and 224;
Positions 59, 89, 129, 179, and 242;
Positions 59, 89, 129, 179, and 254;
Positions 59, 89, 129, 180, and 181;
Positions 59, 89, 129, 180, and 220;
Positions 59, 89, 129, 180, and 224;
Positions 59, 89, 129, 180, and 242;
Positions 59, 89, 129, 180, and 254;
Positions 59, 89, 129, 181, and 220;
Positions 59, 89, 129, 181, and 224;
Positions 59, 89, 129, 181, and 242;
Positions 59, 89, 129, 181, and 254;
Positions 59, 89, 129, 220, and 224;
Positions 59, 89, 129, 220, and 242;
Positions 59, 89, 129, 220, and 254;
Positions 59, 89, 129, 224, and 242;
Positions 59, 89, 129, 224, and 254;
Positions 59, 89, 129, 242, and 254;
Positions 59, 89, 177, 179, and 181;
Positions 59, 89, 177, 179, and 220;
Positions 59, 89, 177, 179, and 224;
Positions 59, 89, 177, 179, and 242;
Positions 59, 89, 177, 179, and 254;
Positions 59, 89, 177, 180, and 181;
Positions 59, 89, 177, 180, and 220;
Positions 59, 89, 177, 180, and 224;
Positions 59, 89, 177, 180, and 242;
Positions 59, 89, 177, 180, and 254;
Positions 59, 89, 177, 181, and 220;
Positions 59, 89, 177, 181, and 224;
Positions 59, 89, 177, 181, and 242;
Positions 59, 89, 177, 181, and 254;
Positions 59, 89, 177, 220, and 224;
Positions 59, 89, 177, 220, and 242;
Positions 59, 89, 177, 220, and 254;
Positions 59, 89, 177, 224, and 242;
Positions 59, 89, 177, 224, and 254;
Positions 59, 89, 177, 242, and 254;
Positions 59, 89, 179, 181, and 220;
Positions 59, 89, 179, 181, and 224;
Positions 59, 89, 179, 181, and 242;
Positions 59, 89, 179, 181, and 254;
Positions 59, 89, 179, 220, and 224;
Positions 59, 89, 179, 220, and 242;
Positions 59, 89, 179, 220, and 254;
Positions 59, 89, 179, 224, and 242;
Positions 59, 89, 179, 224, and 254;
Positions 59, 89, 179, 242, and 254;
Positions 59, 89, 180, 181, and 220;
Positions 59, 89, 180, 181, and 224;
Positions 59, 89, 180, 181, and 242;
Positions 59, 89, 180, 181, and 254;
Positions 59, 89, 180, 220, and 224;
Positions 59, 89, 180, 220, and 242;
Positions 59, 89, 180, 220, and 254;
Positions 59, 89, 180, 224, and 242;
Positions 59, 89, 180, 224, and 254;
Positions 59, 89, 180, 242, and 254;
Positions 59, 89, 181, 220, and 224;
Positions 59, 89, 181, 220, and 242;
Positions 59, 89, 181, 220, and 254;
Positions 59, 89, 181, 224, and 242;
Positions 59, 89, 181, 224, and 254;
Positions 59, 89, 181, 242, and 254;
Positions 59, 89, 220, 224, and 242;
Positions 59, 89, 220, 224, and 254;
Positions 59, 89, 220, 242, and 254;

Positions 59, 89, 224, 242, and 254;
Positions 59, 129, 177, 179, and 181;
Positions 59, 129, 177, 179, and 220;
Positions 59, 129, 177, 179, and 224;
Positions 59, 129, 177, 179, and 242;
Positions 59, 129, 177, 179, and 254;
Positions 59, 129, 177, 180, and 181;
Positions 59, 129, 177, 180, and 220;
Positions 59, 129, 177, 180, and 224;
Positions 59, 129, 177, 180, and 242;
Positions 59, 129, 177, 180, and 254;
Positions 59, 129, 177, 181, and 220;
Positions 59, 129, 177, 181, and 224;
Positions 59, 129, 177, 181, and 242;
Positions 59, 129, 177, 181, and 254;
Positions 59, 129, 177, 220, and 224;
Positions 59, 129, 177, 220, and 242;
Positions 59, 129, 177, 220, and 254;
Positions 59, 129, 177, 224, and 242;
Positions 59, 129, 177, 224, and 254;
Positions 59, 129, 177, 242, and 254;
Positions 59, 129, 179, 181, and 220;
Positions 59, 129, 179, 181, and 224;
Positions 59, 129, 179, 181, and 242;
Positions 59, 129, 179, 181, and 254;
Positions 59, 129, 179, 220, and 224;
Positions 59, 129, 179, 220, and 242;
Positions 59, 129, 179, 220, and 254;
Positions 59, 129, 179, 224, and 242;
Positions 59, 129, 179, 224, and 254;
Positions 59, 129, 179, 242, and 254;
Positions 59, 129, 180, 181, and 220;
Positions 59, 129, 180, 181, and 224;
Positions 59, 129, 180, 181, and 242;
Positions 59, 129, 180, 181, and 254;
Positions 59, 129, 180, 220, and 224;
Positions 59, 129, 180, 220, and 242;
Positions 59, 129, 180, 220, and 254;
Positions 59, 129, 180, 224, and 242;
Positions 59, 129, 180, 224, and 254;
Positions 59, 129, 180, 242, and 254;
Positions 59, 129, 181, 220, and 224;
Positions 59, 129, 181, 220, and 242;
Positions 59, 129, 181, 220, and 254;
Positions 59, 129, 181, 224, and 242;
Positions 59, 129, 181, 224, and 254;
Positions 59, 129, 181, 242, and 254;
Positions 59, 129, 220, 224, and 242;
Positions 59, 129, 220, 224, and 254;
Positions 59, 129, 224, 242, and 254;
Positions 59, 177, 179, 181, and 220;
Positions 59, 177, 179, 181, and 224;
Positions 59, 177, 179, 181, and 242;
Positions 59, 177, 179, 181, and 254;
Positions 59, 177, 179, 220, and 224;
Positions 59, 177, 179, 220, and 242;
Positions 59, 177, 179, 220, and 254;
Positions 59, 177, 179, 224, and 242;
Positions 59, 177, 179, 224, and 254;
Positions 59, 177, 179, 242, and 254;
Positions 59, 177, 180, 181, and 220;
Positions 59, 177, 180, 181, and 224;
Positions 59, 177, 180, 181, and 242;
Positions 59, 177, 180, 181, and 254;
Positions 59, 177, 180, 220, and 224;
Positions 59, 177, 180, 220, and 242;
Positions 59, 177, 180, 220, and 254;
Positions 59, 177, 180, 224, and 242;
Positions 59, 177, 180, 224, and 254;
Positions 59, 177, 180, 242, and 254;
Positions 59, 177, 181, 220, and 224;
Positions 59, 177, 181, 220, and 242;
Positions 59, 177, 181, 220, and 254;
Positions 59, 177, 181, 224, and 242;
Positions 59, 177, 181, 224, and 254;
Positions 59, 177, 181, 242, and 254;
Positions 59, 177, 220, 224, and 242;
Positions 59, 177, 220, 224, and 254;
Positions 59, 177, 224, 242, and 254;
Positions 59, 179, 181, 220, and 224;
Positions 59, 179, 181, 220, and 242;
Positions 59, 179, 181, 220, and 254;
Positions 59, 179, 181, 224, and 242;
Positions 59, 179, 181, 224, and 254;
Positions 59, 179, 181, 242, and 254;
Positions 59, 179, 220, 224, and 242;
Positions 59, 179, 220, 224, and 254;
Positions 59, 179, 220, 242, and 254;
Positions 59, 180, 181, 220, and 224;
Positions 59, 180, 181, 220, and 242;
Positions 59, 180, 181, 220, and 254;
Positions 59, 180, 181, 224, and 242;
Positions 59, 180, 181, 224, and 254;
Positions 59, 180, 181, 242, and 254;
Positions 59, 180, 220, 224, and 242;
Positions 59, 180, 220, 224, and 254;
Positions 59, 180, 220, 242, and 254;
Positions 59, 181, 220, 224, and 242;
Positions 59, 181, 220, 224, and 254;
Positions 59, 181, 220, 242, and 254;
Positions 59, 220, 224, 242, and 254;
Positions 89, 129, 177, 179, and 181;
Positions 89, 129, 177, 179, and 220;
Positions 89, 129, 177, 179, and 224;
Positions 89, 129, 177, 179, and 242;
Positions 89, 129, 177, 179, and 254;
Positions 89, 129, 177, 180, and 181;
Positions 89, 129, 177, 180, and 220;
Positions 89, 129, 177, 180, and 224;
Positions 89, 129, 177, 180, and 242;
Positions 89, 129, 177, 180, and 254;
Positions 89, 129, 177, 181, and 220;
Positions 89, 129, 177, 181, and 224;
Positions 89, 129, 177, 181, and 242;
Positions 89, 129, 177, 181, and 254;
Positions 89, 129, 177, 220, and 224;
Positions 89, 129, 177, 220, and 242;
Positions 89, 129, 177, 220, and 254;
Positions 89, 129, 177, 224, and 242;
Positions 89, 129, 177, 224, and 254;
Positions 89, 129, 177, 242, and 254;
Positions 89, 129, 179, 181, and 220;
Positions 89, 129, 179, 181, and 224;
Positions 89, 129, 179, 181, and 242;
Positions 89, 129, 179, 181, and 254;
Positions 89, 129, 179, 220, and 224;
Positions 89, 129, 179, 220, and 242;
Positions 89, 129, 179, 220, and 254;
Positions 89, 129, 179, 224, and 242;
Positions 89, 129, 179, 224, and 254;
Positions 89, 129, 179, 242, and 254;
Positions 89, 129, 180, 181, and 220;
Positions 89, 129, 180, 181, and 224;
Positions 89, 129, 180, 181, and 242;

Positions 89, 129, 180, 181, and 254;
Positions 89, 129, 180, 220, and 224;
Positions 89, 129, 180, 220, and 242;
Positions 89, 129, 180, 220, and 254;
Positions 89, 129, 180, 224, and 242;
Positions 89, 129, 180, 224, and 254;
Positions 89, 129, 180, 242, and 254;
Positions 89, 129, 181, 220, and 224;
Positions 89, 129, 181, 220, and 242;
Positions 89, 129, 181, 220, and 254;
Positions 89, 129, 181, 224, and 242;
Positions 89, 129, 181, 224, and 254;
Positions 89, 129, 180, 242, and 254;
Positions 89, 177, 179, 181, and 220;
Positions 89, 177, 179, 181, and 224;
Positions 89, 177, 179, 181, and 242;
Positions 89, 177, 179, 181, and 254;
Positions 89, 177, 179, 220, and 224;
Positions 89, 177, 179, 220, and 242;
Positions 89, 177, 179, 220, and 254;
Positions 89, 177, 179, 224, and 242;
Positions 89, 177, 179, 224, and 254;
Positions 89, 177, 179, 242, and 254;
Positions 89, 177, 180, 181, and 220;
Positions 89, 177, 180, 181, and 224;
Positions 89, 177, 180, 181, and 242;
Positions 89, 177, 180, 181, and 254;
Positions 89, 177, 180, 220, and 224;
Positions 89, 177, 180, 220, and 242;
Positions 89, 177, 180, 220, and 254;
Positions 89, 177, 180, 224, and 242;
Positions 89, 177, 180, 224, and 254;
Positions 89, 177, 180, 242, and 254;
Positions 89, 177, 181, 220, and 224;
Positions 89, 177, 181, 220, and 242;
Positions 89, 177, 181, 220, and 254;
Positions 89, 177, 181, 224, and 242;
Positions 89, 177, 181, 224, and 254;
Positions 89, 177, 181, 242, and 254;
Positions 89, 177, 220, 224, and 242;
Positions 89, 177, 220, 224, and 254;
Positions 89, 177, 220, 242, and 254;
Positions 89, 179, 181, 220, and 224;
Positions 89, 179, 181, 220, and 242;
Positions 89, 179, 181, 220, and 254;
Positions 89, 179, 181, 224, and 242;
Positions 89, 179, 181, 242, and 254;
Positions 89, 179, 220, 224, and 242;
Positions 89, 179, 220, 224, and 254;
Positions 89, 179, 220, 242, and 254;
Positions 89, 180, 181, 220, and 224;
Positions 89, 180, 181, 220, and 242;
Positions 89, 180, 181, 220, and 254;
Positions 89, 180, 181, 224, and 242;
Positions 89, 180, 181, 242, and 254;
Positions 89, 180, 220, 224, and 242;
Positions 89, 180, 220, 224, and 254;
Positions 89, 180, 220, 242, and 254;
Positions 89, 181, 220, 224, and 242;
Positions 89, 181, 220, 224, and 254;
Positions 89, 181, 220, 242, and 254;
Positions 89, 220, 224, 242, and 254;
Positions 129, 177, 179, 181, and 220;
Positions 129, 177, 179, 181, and 224;
Positions 129, 177, 179, 181, and 242;
Positions 129, 177, 179, 181, and 254;
Positions 129, 177, 179, 220, and 224;
Positions 129, 177, 179, 220, and 242;
Positions 129, 177, 179, 220, and 254;
Positions 129, 177, 179, 224, and 242;
Positions 129, 177, 179, 224, and 254;
Positions 129, 177, 179, 242, and 254;
Positions 129, 177, 180, 181, and 220;
Positions 129, 177, 180, 181, and 224;
Positions 129, 177, 180, 181, and 242;
Positions 129, 177, 180, 181, and 254;
Positions 129, 177, 180, 220, and 224;
Positions 129, 177, 180, 220, and 242;
Positions 129, 177, 180, 220, and 254;
Positions 129, 177, 180, 224, and 242;
Positions 129, 177, 180, 224, and 254;
Positions 129, 177, 180, 242, and 254;
Positions 129, 177, 181, 220, and 224;
Positions 129, 177, 181, 220, and 242;
Positions 129, 177, 181, 220, and 254;
Positions 129, 177, 181, 224, and 242;
Positions 129, 177, 181, 224, and 254;
Positions 129, 177, 181, 242, and 254;
Positions 129, 179, 181, 220, and 224;
Positions 129, 179, 181, 220, and 242;
Positions 129, 179, 181, 220, and 254;
Positions 129, 179, 181, 224, and 242;
Positions 129, 179, 181, 224, and 254;
Positions 129, 179, 181, 242, and 254;
Positions 129, 179, 220, 224, and 242;
Positions 129, 179, 220, 224, and 254;
Positions 129, 179, 220, 242, and 254;
Positions 129, 179, 224, 242, and 254;
Positions 129, 180, 181, 220, and 224;
Positions 129, 180, 181, 220, and 242;
Positions 129, 180, 181, 220, and 254;
Positions 129, 180, 181, 224, and 242;
Positions 129, 180, 181, 224, and 254;
Positions 129, 180, 181, 242, and 254;
Positions 129, 180, 220, 224, and 242;
Positions 129, 180, 220, 224, and 254;
Positions 129, 180, 220, 242, and 254;
Positions 129, 180, 224, 242, and 254;
Positions 129, 181, 220, 224, and 242;
Positions 129, 181, 220, 224, and 254;
Positions 129, 181, 220, 242, and 254;
Positions 129, 181, 224, 242, and 254;
Positions 129, 220, 224, 242, and 254;
Positions 177, 179, 181, 220, and 224;
Positions 177, 179, 181, 220, and 242;
Positions 177, 179, 181, 220, and 254;
Positions 177, 179, 181, 224, and 242;
Positions 177, 179, 181, 224, and 254;
Positions 177, 179, 181, 242, and 254;
Positions 177, 179, 220, 224, and 242;
Positions 177, 179, 220, 224, and 254;
Positions 177, 179, 220, 242, and 254;
Positions 177, 179, 224, 242, and 254;
Positions 177, 180, 181, 220, and 224;
Positions 177, 180, 181, 220, and 242;
Positions 177, 180, 181, 220, and 254;
Positions 177, 180, 181, 224, and 242;
Positions 177, 180, 181, 224, and 254;
Positions 177, 180, 181, 242, and 254;
Positions 177, 180, 220, 224, and 242;
Positions 177, 180, 220, 224, and 254;
Positions 177, 180, 224, 242, and 254;
Positions 177, 181, 220, 224, and 242;
Positions 177, 181, 220, 224, and 254;

Positions 177, 181, 224, 242, and 254;
Positions 177, 220, 224, 242, and 254;
Positions 179, 181, 220, 224, and 242;
Positions 179, 181, 220, 224, and 254;
Positions 179, 181, 220, 242, and 254;
Positions 179, 181, 224, 242, and 254;
Positions 179, 220, 224, 242, and 254;
Positions 180, 181, 220, 224, and 242;
Positions 180, 181, 220, 224, and 254;
Positions 180, 181, 220, 242, and 254;
Positions 180, 181, 224, 242, and 254;
Positions 180, 220, 224, 242, and 254; and
Positions 181, 220, 224, 242 and 254.

Paragraph 38. The variant of any of paragraphs 1-31, comprising a substitution at six positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, in particular, at the positions corresponding to positions 129, 177, 179, 208, 242, and 284 or positions 129, 177, 179, 220, 224, and 254.

Paragraph 39. The variant of paragraph 38, wherein the six positions are selected from the group consisting of:
Positions 59, 89, 129, 177, 179, and 181;
Positions 59, 89, 129, 177, 179, and 220;
Positions 59, 89, 129, 177, 179, and 224;
Positions 59, 89, 129, 177, 179, and 242;
Positions 59, 89, 129, 177, 179, and 254;
Positions 59, 89, 129, 177, 180, and 181;
Positions 59, 89, 129, 177, 180, and 220;
Positions 59, 89, 129, 177, 180, and 224;
Positions 59, 89, 129, 177, 180, and 242;
Positions 59, 89, 129, 177, 180, and 254;
Positions 59, 89, 129, 177, 181, and 220;
Positions 59, 89, 129, 177, 181, and 224;
Positions 59, 89, 129, 177, 181, and 242;
Positions 59, 89, 129, 177, 181, and 254;
Positions 59, 89, 129, 177, 220, and 224;
Positions 59, 89, 129, 177, 220, and 242;
Positions 59, 89, 129, 177, 220, and 254;
Positions 59, 89, 129, 177, 224, and 242;
Positions 59, 89, 129, 177, 224, and 254;
Positions 59, 89, 129, 177, 242, and 254;
Positions 59, 89, 129, 179, 181, and 220;
Positions 59, 89, 129, 179, 181, and 224;
Positions 59, 89, 129, 179, 181, and 242;
Positions 59, 89, 129, 179, 181, and 254;
Positions 59, 89, 129, 179, 220, and 224;
Positions 59, 89, 129, 179, 220, and 242;
Positions 59, 89, 129, 179, 220, and 254;
Positions 59, 89, 129, 179, 224, and 242;
Positions 59, 89, 129, 179, 224, and 254;
Positions 59, 89, 129, 179, 242, and 254;
Positions 59, 89, 129, 180, 181, and 220;
Positions 59, 89, 129, 180, 181, and 224;
Positions 59, 89, 129, 180, 181, and 242;
Positions 59, 89, 129, 180, 181, and 254;
Positions 59, 89, 129, 180, 220, and 224;
Positions 59, 89, 129, 180, 220, and 242;
Positions 59, 89, 129, 180, 220, and 254;
Positions 59, 89, 129, 180, 224, and 242;
Positions 59, 89, 129, 180, 224, and 254;
Positions 59, 89, 129, 180, 242, and 254;
Positions 59, 89, 129, 181, 220, and 224;
Positions 59, 89, 129, 181, 220, and 242;
Positions 59, 89, 129, 181, 220, and 254;
Positions 59, 89, 129, 181, 224, and 242;
Positions 59, 89, 129, 181, 224, and 254;
Positions 59, 89, 129, 181, 242, and 254;
Positions 59, 89, 129, 220, 224, and 242;
Positions 59, 89, 129, 220, 224, and 254;
Positions 59, 89, 129, 220, 242, and 254;
Positions 59, 89, 129, 224, 242, and 254;
Positions 59, 89, 177, 179, 181, and 220;
Positions 59, 89, 177, 179, 181, and 224;
Positions 59, 89, 177, 179, 181, and 242;
Positions 59, 89, 177, 179, 181, and 254;
Positions 59, 89, 177, 179, 220, and 224;
Positions 59, 89, 177, 179, 220, and 242;
Positions 59, 89, 177, 179, 220, and 254;
Positions 59, 89, 177, 179, 224, and 242;
Positions 59, 89, 177, 179, 224, and 254;
Positions 59, 89, 177, 179, 242, and 254;
Positions 59, 89, 177, 180, 181, and 220;
Positions 59, 89, 177, 180, 181, and 224;
Positions 59, 89, 177, 180, 181, and 242;
Positions 59, 89, 177, 180, 181, and 254;
Positions 59, 89, 177, 180, 220, and 224;
Positions 59, 89, 177, 180, 220, and 242;
Positions 59, 89, 177, 180, 220, and 254;
Positions 59, 89, 177, 180, 224, and 242;
Positions 59, 89, 177, 180, 224, and 254;
Positions 59, 89, 177, 180, 242, and 254;
Positions 59, 89, 177, 181, 220, and 224;
Positions 59, 89, 177, 181, 220, and 242;
Positions 59, 89, 177, 181, 220, and 254;
Positions 59, 89, 177, 181, 224, and 242;
Positions 59, 89, 177, 181, 224, and 254;
Positions 59, 89, 177, 181, 242, and 254;
Positions 59, 89, 177, 220, 224, and 242;
Positions 59, 89, 177, 220, 224, and 254;
Positions 59, 89, 177, 220, 242, and 254;
Positions 59, 89, 179, 181, 220, and 224;
Positions 59, 89, 179, 181, 220, and 242;
Positions 59, 89, 179, 181, 220, and 254;
Positions 59, 89, 179, 181, 224, and 242;
Positions 59, 89, 179, 181, 224, and 254;
Positions 59, 89, 179, 181, 242, and 254;
Positions 59, 89, 179, 220, 224, and 242;
Positions 59, 89, 179, 220, 224, and 254;
Positions 59, 89, 179, 220, 242, and 254;
Positions 59, 89, 180, 181, 220, and 224;
Positions 59, 89, 180, 181, 220, and 242;
Positions 59, 89, 180, 181, 220, and 254;
Positions 59, 89, 180, 181, 224, and 242;
Positions 59, 89, 180, 181, 224, and 254;
Positions 59, 89, 180, 181, 242, and 254;
Positions 59, 89, 180, 220, 224, and 242;
Positions 59, 89, 180, 220, 224, and 254;
Positions 59, 89, 180, 220, 242, and 254;
Positions 59, 89, 181, 220, 224, and 242;
Positions 59, 89, 181, 220, 224, and 254;
Positions 59, 89, 181, 220, 242, and 254;
Positions 59, 89, 220, 224, 242, and 254;
Positions 59, 129, 177, 179, 181, and 220;
Positions 59, 129, 177, 179, 181, and 224;
Positions 59, 129, 177, 179, 181, and 242;
Positions 59, 129, 177, 179, 181, and 254;
Positions 59, 129, 177, 179, 208, and 284;
Positions 59, 129, 177, 179, 220, and 224;
Positions 59, 129, 177, 179, 220, and 242;
Positions 59, 129, 177, 179, 220, and 254;
Positions 59, 129, 177, 179, 224, and 242;
Positions 59, 129, 177, 179, 224, and 254;
Positions 59, 129, 177, 179, 242, and 254;

Positions 59, 129, 177, 180, 181, and 220;
Positions 59, 129, 177, 180, 181, and 224;
Positions 59, 129, 177, 180, 181, and 242;
Positions 59, 129, 177, 180, 181, and 254;
Positions 59, 129, 177, 180, 220, and 224;
Positions 59, 129, 177, 180, 220, and 242;
Positions 59, 129, 177, 180, 220, and 254;
Positions 59, 129, 177, 180, 224, and 242;
Positions 59, 129, 177, 180, 224, and 254;
Positions 59, 129, 177, 180, 242, and 254;
Positions 59, 129, 177, 181, 220, and 224;
Positions 59, 129, 177, 181, 220, and 242;
Positions 59, 129, 177, 181, 220, and 254;
Positions 59, 129, 177, 181, 224, and 242;
Positions 59, 129, 177, 181, 224, and 254;
Positions 59, 129, 177, 181, 242, and 254;
Positions 59, 129, 177, 220, 224, and 242;
Positions 59, 129, 177, 220, 224, and 254;
Positions 59, 129, 177, 224, 242, and 254;
Positions 59, 129, 179, 181, 220, and 224;
Positions 59, 129, 179, 181, 220, and 242;
Positions 59, 129, 179, 181, 220, and 254;
Positions 59, 129, 179, 220, 224, and 242;
Positions 59, 129, 179, 220, 224, and 254;
Positions 59, 129, 179, 220, 242, and 254;
Positions 59, 129, 179, 224, 242, and 254;
Positions 59, 129, 180, 181, 220, and 224;
Positions 59, 129, 180, 181, 220, and 242;
Positions 59, 129, 180, 181, 220, and 254;
Positions 59, 129, 180, 220, 224, and 242;
Positions 59, 129, 180, 220, 224, and 254;
Positions 59, 129, 180, 220, 242, and 254;
Positions 59, 129, 180, 224, 242, and 254;
Positions 59, 129, 181, 220, 224, and 242;
Positions 59, 129, 181, 220, 224, and 254;
Positions 59, 129, 181, 220, 242, and 254;
Positions 59, 129, 181, 224, 242, and 254;
Positions 59, 129, 220, 224, 242, and 254;
Positions 59, 177, 179, 181, 220, and 224;
Positions 59, 177, 179, 181, 220, and 242;
Positions 59, 177, 179, 181, 220, and 254;
Positions 59, 177, 179, 181, 224, and 242;
Positions 59, 177, 179, 181, 224, and 254;
Positions 59, 177, 179, 181, 242, and 254;
Positions 59, 177, 179, 220, 224, and 242;
Positions 59, 177, 179, 220, 224, and 254;
Positions 59, 177, 179, 220, 242, and 254;
Positions 59, 177, 179, 224, 242, and 254;
Positions 59, 177, 180, 181, 220, and 224;
Positions 59, 177, 180, 181, 220, and 242;
Positions 59, 177, 180, 181, 220, and 254;
Positions 59, 177, 180, 181, 224, and 242;
Positions 59, 177, 180, 181, 224, and 254;
Positions 59, 177, 180, 181, 242, and 254;
Positions 59, 177, 180, 220, 224, and 242;
Positions 59, 177, 180, 220, 224, and 254;
Positions 59, 177, 180, 220, 242, and 254;
Positions 59, 177, 180, 224, 242, and 254;
Positions 59, 177, 181, 220, 224, and 242;
Positions 59, 177, 181, 220, 224, and 254;
Positions 59, 177, 181, 220, 242, and 254;
Positions 59, 177, 181, 224, 242, and 254;
Positions 59, 177, 220, 224, 242, and 254;
Positions 59, 179, 181, 220, 224, and 242;
Positions 59, 179, 181, 220, 224, and 254;
Positions 59, 179, 181, 220, 242, and 254;
Positions 59, 179, 181, 224, 242, and 254;
Positions 59, 179, 220, 224, 242, and 254;
Positions 59, 180, 181, 220, 224, and 242;
Positions 59, 180, 181, 220, 224, and 254;
Positions 59, 180, 181, 220, 242, and 254;
Positions 59, 180, 181, 224, 242, and 254;
Positions 59, 180, 220, 224, 242, and 254;
Positions 59, 181, 220, 224, 242, and 254;
Positions 59, 208, 220, 224, 254, and 284;
Positions 89, 129, 177, 179, 181, and 220;
Positions 89, 129, 177, 179, 181, and 224;
Positions 89, 129, 177, 179, 181, and 242;
Positions 89, 129, 177, 179, 181, and 254;
Positions 89, 129, 177, 179, 220, and 224;
Positions 89, 129, 177, 179, 220, and 242;
Positions 89, 129, 177, 179, 220, and 254;
Positions 89, 129, 177, 179, 224, and 242;
Positions 89, 129, 177, 179, 224, and 254;
Positions 89, 129, 177, 179, 242, and 254;
Positions 89, 129, 177, 180, 181, and 220;
Positions 89, 129, 177, 180, 181, and 224;
Positions 89, 129, 177, 180, 181, and 242;
Positions 89, 129, 177, 180, 181, and 254;
Positions 89, 129, 177, 180, 220, and 224;
Positions 89, 129, 177, 180, 220, and 242;
Positions 89, 129, 177, 180, 220, and 254;
Positions 89, 129, 177, 180, 224, and 242;
Positions 89, 129, 177, 180, 224, and 254;
Positions 89, 129, 177, 180, 242, and 254;
Positions 89, 129, 177, 181, 220, and 224;
Positions 89, 129, 177, 181, 220, and 242;
Positions 89, 129, 177, 181, 220, and 254;
Positions 89, 129, 177, 181, 224, and 242;
Positions 89, 129, 177, 181, 224, and 254;
Positions 89, 129, 177, 181, 242, and 254;
Positions 89, 129, 177, 220, 224, and 242;
Positions 89, 129, 177, 220, 224, and 254;
Positions 89, 129, 177, 220, 242, and 254;
Positions 89, 129, 177, 224, 242, and 254;
Positions 89, 129, 179, 181, 220, and 224;
Positions 89, 129, 179, 181, 220, and 242;
Positions 89, 129, 179, 181, 220, and 254;
Positions 89, 129, 179, 181, 224, and 242;
Positions 89, 129, 179, 181, 224, and 254;
Positions 89, 129, 179, 181, 242, and 254;
Positions 89, 129, 179, 220, 224, and 242;
Positions 89, 129, 179, 220, 224, and 254;
Positions 89, 129, 179, 220, 242, and 254;
Positions 89, 129, 179, 224, 242, and 254;
Positions 89, 129, 180, 220, 224, and 242;
Positions 89, 129, 180, 220, 224, and 254;
Positions 89, 129, 180, 220, 242, and 254;
Positions 89, 129, 180, 224, 242, and 254;
Positions 89, 129, 181, 220, 224, and 242;
Positions 89, 129, 181, 220, 224, and 254;
Positions 89, 129, 181, 220, 242, and 254;
Positions 89, 129, 181, 224, 242, and 254;
Positions 89, 129, 220, 224, 242, and 254;
Positions 89, 177, 179, 181, 220, and 224;
Positions 89, 177, 179, 181, 220, and 242;
Positions 89, 177, 179, 181, 220, and 254;
Positions 89, 177, 179, 181, 224, and 242;
Positions 89, 177, 179, 181, 224, and 254;
Positions 89, 177, 179, 181, 242, and 254;
Positions 89, 177, 179, 220, 224, and 242;
Positions 89, 177, 179, 220, 224, and 254;
Positions 89, 177, 179, 220, 242, and 254;
Positions 89, 177, 179, 224, 242, and 254;

Positions 89, 177, 180, 181, 220, and 224;
Positions 89, 177, 180, 181, 220, and 242;
Positions 89, 177, 180, 181, 220, and 254;
Positions 89, 177, 180, 181, 224, and 242;
Positions 89, 177, 180, 181, 224, and 254;
Positions 89, 177, 180, 181, 242, and 254;
Positions 89, 177, 180, 220, 224, and 242;
Positions 89, 177, 180, 220, 224, and 254;
Positions 89, 177, 180, 220, 242, and 254;
Positions 89, 177, 180, 224, 242, and 254;
Positions 89, 177, 181, 220, 224, and 242;
Positions 89, 177, 181, 220, 224, and 254;
Positions 89, 177, 181, 220, 242, and 254;
Positions 89, 177, 181, 224, 242, and 254;
Positions 89, 177, 220, 224, 242, and 254;
Positions 89, 179, 181, 220, 224, and 242;
Positions 89, 179, 181, 220, 224, and 254;
Positions 89, 179, 181, 220, 242, and 254;
Positions 89, 179, 181, 224, 242, and 254;
Positions 89, 179, 220, 224, 242, and 254;
Positions 89, 180, 181, 220, 224, and 242;
Positions 89, 180, 181, 220, 224, and 254;
Positions 89, 180, 181, 220, 242, and 254;
Positions 89, 180, 181, 224, 242, and 254;
Positions 89, 180, 220, 224, 242, and 254;
Positions 89, 181, 220, 224, 242, and 254;
Positions 129, 177, 179, 181, 220, and 224;
Positions 129, 177, 179, 181, 220, and 242;
Positions 129, 177, 179, 181, 220, and 254;
Positions 129, 177, 179, 181, 224, and 242;
Positions 129, 177, 179, 181, 224, and 254;
Positions 129, 177, 179, 181, 242, and 254;
Positions 129, 177, 179, 220, 224, and 242;
Positions 129, 177, 179, 220, 224, and 254;
Positions 129, 177, 179, 220, 242, and 254;
Positions 129, 177, 179, 224, 242, and 254;
Positions 129, 177, 180, 181, 220, and 224;
Positions 129, 177, 180, 181, 220, and 242;
Positions 129, 177, 180, 181, 220, and 254;
Positions 129, 177, 180, 181, 224, and 242;
Positions 129, 177, 180, 181, 224, and 254;
Positions 129, 177, 180, 181, 242, and 254;
Positions 129, 177, 180, 220, 224, and 242;
Positions 129, 177, 180, 220, 224, and 254;
Positions 129, 177, 180, 220, 242, and 254;
Positions 129, 177, 180, 224, 242, and 254;
Positions 129, 177, 181, 220, 224, and 242;
Positions 129, 177, 181, 220, 224, and 254;
Positions 129, 177, 181, 220, 242, and 254;
Positions 129, 177, 181, 224, 242, and 254;
Positions 129, 177, 200, 224, 242, and 254;
Positions 129, 179, 181, 220, 224, and 242;
Positions 129, 179, 181, 220, 224, and 254;
Positions 129, 179, 181, 220, 242, and 254;
Positions 129, 179, 181, 224, 242, and 254;
Positions 129, 179, 220, 224, 242, and 254;
Positions 129, 180, 181, 220, 224, and 242;
Positions 129, 180, 181, 220, 224, and 254;
Positions 129, 180, 181, 220, 242, and 254;
Positions 129, 180, 181, 224, 242, and 254;
Positions 129, 180, 220, 224, 242, and 254;
Positions 129, 181, 220, 224, 242, and 254;
Positions 177, 179, 181, 220, 224, and 242;
Positions 177, 179, 181, 220, 224, and 254;
Positions 177, 179, 220, 224, 242, and 254;
Positions 177, 180, 181, 220, 224, and 242;
Positions 177, 180, 181, 220, 224, and 254;
Positions 177, 180, 181, 224, 242, and 254;
Positions 177, 180, 220, 224, 242, and 254;
Positions 177, 181, 220, 224, 242, and 254;
Positions 179, 181, 220, 224, 242, and 254; and
Positions 180, 181, 220, 224, 242, and 254.

Paragraph 40. The variant of any of paragraphs 1-31, comprising a substitution at seven positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

Paragraph 41. The variant of paragraph 40, wherein the seven positions are selected from the group consisting of:
Positions 59, 89, 129, 177, 179, 181, and 220;
Positions 59, 89, 129, 177, 179, 181, and 224;
Positions 59, 89, 129, 177, 179, 181, and 242;
Positions 59, 89, 129, 177, 179, 181, and 254;
Positions 59, 89, 129, 177, 179, 220, and 224;
Positions 59, 89, 129, 177, 179, 220, and 242;
Positions 59, 89, 129, 177, 179, 220, and 254;
Positions 59, 89, 129, 177, 179, 224, and 242;
Positions 59, 89, 129, 177, 179, 224, and 254;
Positions 59, 89, 129, 177, 179, 242, and 254;
Positions 59, 89, 129, 177, 180, 181, and 220;
Positions 59, 89, 129, 177, 180, 181, and 224;
Positions 59, 89, 129, 177, 180, 181, and 242;
Positions 59, 89, 129, 177, 180, 181, and 254;
Positions 59, 89, 129, 177, 180, 220, and 224;
Positions 59, 89, 129, 177, 180, 220, and 242;
Positions 59, 89, 129, 177, 180, 220, and 254;
Positions 59, 89, 129, 177, 180, 224, and 242;
Positions 59, 89, 129, 177, 180, 224, and 254;
Positions 59, 89, 129, 177, 180, 242, and 254;
Positions 59, 89, 129, 177, 181, 220, and 224;
Positions 59, 89, 129, 177, 181, 220, and 242;
Positions 59, 89, 129, 177, 181, 220, and 254;
Positions 59, 89, 129, 177, 181, 224, and 242;
Positions 59, 89, 129, 177, 181, 224, and 254;
Positions 59, 89, 129, 177, 181, 242, and 254;
Positions 59, 89, 129, 177, 220, 224, and 242;
Positions 59, 89, 129, 177, 220, 224, and 254;
Positions 59, 89, 129, 177, 224, 242, and 254;
Positions 59, 89, 129, 179, 181, 220, and 224;
Positions 59, 89, 129, 179, 181, 220, and 242;
Positions 59, 89, 129, 179, 181, 220, and 254;
Positions 59, 89, 129, 179, 181, 224, and 242;
Positions 59, 89, 129, 179, 181, 224, and 254;
Positions 59, 89, 129, 179, 181, 242, and 254;
Positions 59, 89, 129, 179, 220, 224, and 242;
Positions 59, 89, 129, 179, 220, 224, and 254;
Positions 59, 89, 129, 179, 220, 242, and 254;
Positions 59, 89, 129, 179, 224, 242, and 254;
Positions 59, 89, 129, 180, 181, 220, and 224;
Positions 59, 89, 129, 180, 181, 220, and 242;
Positions 59, 89, 129, 180, 181, 220, and 254;
Positions 59, 89, 129, 180, 181, 224, and 242;
Positions 59, 89, 129, 180, 181, 224, and 254;
Positions 59, 89, 129, 180, 181, 242, and 254;
Positions 59, 89, 129, 180, 220, 224, and 242;
Positions 59, 89, 129, 180, 220, 224, and 254;
Positions 59, 89, 129, 180, 220, 242, and 254;
Positions 59, 89, 129, 180, 224, 242, and 254;
Positions 59, 89, 129, 181, 220, 224, and 242;
Positions 59, 89, 129, 181, 220, 224, and 254;
Positions 59, 89, 129, 181, 220, 242, and 254;
Positions 59, 89, 129, 181, 224, 242, and 254;
Positions 59, 89, 129, 220, 224, 242, and 254;

Positions 59, 89, 177, 179, 181, 220, and 224;
Positions 59, 89, 177, 179, 181, 220, and 242;
Positions 59, 89, 177, 179, 181, 220, and 254;
Positions 59, 89, 177, 179, 181, 224, and 242;
Positions 59, 89, 177, 179, 181, 224, and 254;
Positions 59, 89, 177, 179, 181, 242, and 254;
Positions 59, 89, 177, 179, 220, 224, and 242;
Positions 59, 89, 177, 179, 220, 224, and 254;
Positions 59, 89, 177, 179, 224, 242, and 254;
Positions 59, 89, 177, 180, 181, 220, and 224;
Positions 59, 89, 177, 180, 181, 220, and 242;
Positions 59, 89, 177, 180, 181, 220, and 254;
Positions 59, 89, 177, 180, 181, 224, and 242;
Positions 59, 89, 177, 180, 181, 224, and 254;
Positions 59, 89, 177, 180, 181, 242, and 254;
Positions 59, 89, 177, 180, 220, 224, and 242;
Positions 59, 89, 177, 180, 220, 224, and 254;
Positions 59, 89, 177, 180, 224, 242, and 254;
Positions 59, 89, 177, 181, 220, 224, and 242;
Positions 59, 89, 177, 181, 220, 224, and 254;
Positions 59, 89, 177, 181, 220, 242, and 254;
Positions 59, 89, 177, 181, 224, 242, and 254;
Positions 59, 89, 177, 220, 224, 242, and 254;
Positions 59, 89, 179, 181, 220, 224, and 242;
Positions 59, 89, 179, 181, 220, 224, and 254;
Positions 59, 89, 179, 181, 220, 242, and 254;
Positions 59, 89, 179, 220, 224, 242, and 254;
Positions 59, 89, 180, 181, 220, 224, and 242;
Positions 59, 89, 180, 181, 220, 224, and 254;
Positions 59, 89, 180, 181, 220, 242, and 254;
Positions 59, 89, 180, 220, 224, 242, and 254;
Positions 59, 89, 181, 220, 224, 242, and 254;
Positions 59, 129, 177, 179, 181, 220, and 224;
Positions 59, 129, 177, 179, 181, 220, and 242;
Positions 59, 129, 177, 179, 181, 220, and 254;
Positions 59, 129, 177, 179, 181, 224, and 242;
Positions 59, 129, 177, 179, 181, 224, and 254;
Positions 59, 129, 177, 179, 181, 242, and 254;
Positions 59, 129, 177, 179, 220, 224, and 242;
Positions 59, 129, 177, 179, 220, 224, and 254;
Positions 59, 129, 177, 179, 220, 242, and 254;
Positions 59, 129, 177, 179, 224, 242, and 254;
Positions 59, 129, 177, 180, 181, 220, and 224;
Positions 59, 129, 177, 180, 181, 220, and 242;
Positions 59, 129, 177, 180, 181, 220, and 254;
Positions 59, 129, 177, 180, 181, 224, and 242;
Positions 59, 129, 177, 180, 181, 224, and 254;
Positions 59, 129, 177, 180, 181, 242, and 254;
Positions 59, 129, 177, 180, 220, 224, and 242;
Positions 59, 129, 177, 180, 220, 224, and 254;
Positions 59, 129, 177, 180, 220, 242, and 254;
Positions 59, 129, 177, 180, 224, 242, and 254;
Positions 59, 129, 177, 181, 220, 224, and 242;
Positions 59, 129, 177, 181, 220, 224, and 254;
Positions 59, 129, 177, 181, 220, 242, and 254;
Positions 59, 129, 177, 181, 224, 242, and 254;
Positions 59, 129, 177, 220, 224, 242, and 254;
Positions 59, 177, 179, 181, 220, 224, and 242;
Positions 59, 177, 179, 181, 220, 224, and 254;
Positions 59, 177, 179, 181, 220, 242, and 254;
Positions 59, 177, 179, 181, 224, 242, and 254;
Positions 59, 177, 179, 220, 224, 242, and 254;
Positions 59, 177, 180, 181, 220, 224, and 242;
Positions 59, 177, 180, 181, 220, 224, and 254;
Positions 59, 177, 180, 181, 220, 242, and 254;
Positions 59, 177, 180, 181, 224, 242, and 254;
Positions 59, 177, 180, 220, 224, 242, and 254;
Positions 59, 177, 181, 220, 224, 242, and 254;
Positions 59, 179, 181, 220, 224, 242, and 254;
Positions 59, 180, 181, 220, 224, 242, and 254;
Positions 89, 129, 177, 179, 181, 220, and 224;
Positions 89, 129, 177, 179, 181, 220, and 242;
Positions 89, 129, 177, 179, 181, 220, and 254;
Positions 89, 129, 177, 179, 181, 224, and 242;
Positions 89, 129, 177, 179, 181, 224, and 254;
Positions 89, 129, 177, 179, 181, 242, and 254;
Positions 89, 129, 177, 179, 220, 224, and 242;
Positions 89, 129, 177, 179, 220, 224, and 254;
Positions 89, 129, 177, 179, 220, 242, and 254;
Positions 89, 129, 177, 179, 224, 242, and 254;
Positions 89, 129, 177, 180, 181, 220, and 224;
Positions 89, 129, 177, 180, 181, 220, and 242;
Positions 89, 129, 177, 180, 181, 220, and 254;
Positions 89, 129, 177, 180, 181, 224, and 242;
Positions 89, 129, 177, 180, 181, 224, and 254;
Positions 89, 129, 177, 180, 181, 242, and 254;
Positions 89, 129, 177, 180, 220, 224, and 242;
Positions 89, 129, 177, 180, 220, 224, and 254;
Positions 89, 129, 177, 180, 220, 242, and 254;
Positions 89, 129, 177, 180, 224, 242, and 254;
Positions 89, 129, 177, 181, 220, 224, and 242;
Positions 89, 129, 177, 181, 220, 224, and 254;
Positions 89, 129, 177, 181, 220, 242, and 254;
Positions 89, 129, 177, 181, 224, 242, and 254;
Positions 89, 129, 177, 220, 224, 242, and 254;
Positions 89, 129, 179, 181, 220, 224, and 242;
Positions 89, 129, 179, 181, 220, 224, and 254;
Positions 89, 129, 179, 181, 220, 242, and 254;
Positions 89, 129, 179, 181, 224, 242, and 254;
Positions 89, 129, 179, 220, 224, 242, and 254;
Positions 89, 129, 180, 181, 220, 224, and 242;
Positions 89, 129, 180, 181, 220, 224, and 254;
Positions 89, 129, 180, 181, 220, 242, and 254;
Positions 89, 129, 180, 181, 224, 242, and 254;
Positions 89, 129, 180, 220, 224, 242, and 254;
Positions 89, 129, 181, 220, 224, 242, and 254;
Positions 89, 177, 179, 181, 220, 224, and 242;
Positions 89, 177, 179, 181, 220, 224, and 254;
Positions 89, 177, 179, 181, 220, 242, and 254;
Positions 89, 177, 179, 181, 224, 242, and 254;
Positions 89, 177, 179, 220, 224, 242, and 254;
Positions 89, 177, 180, 181, 220, 224, and 242;
Positions 89, 177, 180, 181, 220, 224, and 254;
Positions 89, 177, 180, 181, 220, 242, and 254;
Positions 89, 177, 180, 181, 224, 242, and 254;
Positions 89, 177, 180, 220, 224, 242, and 254;
Positions 89, 177, 181, 220, 224, 242, and 254;
Positions 89, 179, 181, 220, 224, 242, and 254;
Positions 89, 180, 181, 220, 224, 242, and 254;
Positions 129, 177, 179, 181, 220, 224, and 242;
Positions 129, 177, 179, 181, 220, 224, and 254;
Positions 129, 177, 179, 181, 220, 242, and 254;
Positions 129, 177, 179, 181, 224, 242, and 254;
Positions 129, 177, 179, 220, 224, 242, and 254;
Positions 129, 177, 180, 181, 220, 224, and 242;
Positions 129, 177, 180, 181, 220, 224, and 254;
Positions 129, 177, 180, 181, 220, 242, and 254;
Positions 129, 177, 180, 181, 224, 242, and 254;
Positions 129, 177, 180, 220, 224, 242, and 254;
Positions 129, 177, 181, 220, 224, 242, and 254;
Positions 129, 179, 181, 220, 224, 242, and 254;
Positions 129, 180, 181, 220, 224, 242, and 254;
Positions 177, 179, 181, 220, 224, 242, and 254; and
Positions 177, 180, 181, 220, 224, 242, and 254.

Paragraph 42. The variant of any of paragraphs 1-31, comprising a substitution at eight positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

Paragraph 43. The variant of paragraph 42, wherein the eight positions are selected from the group consisting of:
Positions 59, 89, 129, 177, 179, 181, 220, and 224;
Positions 59, 89, 129, 177, 179, 181, 220, and 242;
Positions 59, 89, 129, 177, 179, 181, 220, and 254;
Positions 59, 89, 129, 177, 179, 181, 224, and 242;
Positions 59, 89, 129, 177, 179, 181, 224, and 254;
Positions 59, 89, 129, 177, 179, 181, 242, and 254;
Positions 59, 89, 129, 177, 179, 220, 224, and 242;
Positions 59, 89, 129, 177, 179, 220, 224, and 254;
Positions 59, 89, 129, 177, 179, 220, 242, and 254;
Positions 59, 89, 129, 177, 179, 224, 242, and 254;
Positions 59, 89, 129, 177, 180, 181, 220, and 224;
Positions 59, 89, 129, 177, 180, 181, 220, and 242;
Positions 59, 89, 129, 177, 180, 181, 220, and 254;
Positions 59, 89, 129, 177, 180, 181, 224, and 242;
Positions 59, 89, 129, 177, 180, 181, 224, and 254;
Positions 59, 89, 129, 177, 180, 181, 242, and 254;
Positions 59, 89, 129, 177, 180, 220, 224, and 242;
Positions 59, 89, 129, 177, 180, 220, 224, and 254;
Positions 59, 89, 129, 177, 180, 220, 242, and 254;
Positions 59, 89, 129, 177, 180, 224, 242, and 254;
Positions 59, 89, 129, 177, 181, 220, 224, and 242;
Positions 59, 89, 129, 177, 181, 220, 224, and 254;
Positions 59, 89, 129, 177, 181, 220, 242, and 254;
Positions 59, 89, 129, 177, 181, 224, 242, and 254;
Positions 59, 89, 129, 177, 220, 224, 242, and 254;
Positions 59, 89, 129, 179, 181, 220, 224, and 242;
Positions 59, 89, 129, 179, 181, 220, 224, and 254;
Positions 59, 89, 129, 179, 181, 220, 242, and 254;
Positions 59, 89, 129, 179, 181, 224, 242, and 254;
Positions 59, 89, 129, 179, 220, 224, 242, and 254;
Positions 59, 89, 129, 180, 181, 220, 224, and 242;
Positions 59, 89, 129, 180, 181, 220, 224, and 254;
Positions 59, 89, 129, 180, 181, 220, 242, and 254;
Positions 59, 89, 129, 180, 181, 224, 242, and 254;
Positions 59, 89, 129, 180, 220, 224, 242, and 254;
Positions 59, 89, 129, 181, 220, 224, 242, and 254;
Positions 59, 89, 177, 179, 181, 220, 224, and 242;
Positions 59, 89, 177, 179, 181, 220, 224, and 254;
Positions 59, 89, 177, 179, 181, 220, 242, and 254;
Positions 59, 89, 177, 179, 181, 224, 242, and 254;
Positions 59, 89, 177, 179, 220, 224, 242, and 254;
Positions 59, 89, 177, 180, 181, 220, 224, and 242;
Positions 59, 89, 177, 180, 181, 220, 224, and 254;
Positions 59, 89, 177, 180, 181, 220, 242, and 254;
Positions 59, 89, 177, 180, 181, 224, 242, and 254;
Positions 59, 89, 177, 180, 220, 224, 242, and 254;
Positions 59, 89, 177, 181, 220, 224, 242, and 254;
Positions 59, 89, 179, 181, 220, 224, 242, and 254;
Positions 59, 89, 180, 181, 220, 224, 242, and 254;
Positions 59, 129, 177, 179, 181, 220, 224, and 242;
Positions 59, 129, 177, 179, 181, 220, 224, and 254;
Positions 59, 129, 177, 179, 181, 224, 242, and 254;
Positions 59, 129, 177, 179, 220, 224, 242, and 254;
Positions 59, 129, 177, 180, 181, 220, 224, and 242;
Positions 59, 129, 177, 180, 181, 220, 224, and 254;
Positions 59, 129, 177, 180, 181, 224, 242, and 254;
Positions 59, 129, 177, 180, 220, 224, 242, and 254;
Positions 59, 129, 177, 181, 220, 224, 242, and 254;
Positions 59, 129, 179, 181, 220, 224, 242, and 254;
Positions 59, 129, 180, 181, 220, 224, 242, and 254;
Positions 59, 177, 179, 181, 220, 224, 242, and 254;
Positions 59, 177, 180, 181, 220, 224, 242, and 254;
Positions 89, 129, 177, 179, 181, 220, 224, and 242;
Positions 89, 129, 177, 179, 181, 220, 224, and 254;
Positions 89, 129, 177, 179, 181, 224, 242, and 254;
Positions 89, 129, 177, 179, 220, 224, 242, and 254;
Positions 89, 129, 177, 180, 181, 220, 224, and 242;
Positions 89, 129, 177, 180, 181, 220, 224, and 254;
Positions 89, 129, 177, 180, 181, 224, 242, and 254;
Positions 89, 129, 177, 180, 220, 224, 242, and 254;
Positions 89, 129, 177, 181, 220, 224, 242, and 254;
Positions 129, 177, 179, 181, 220, 224, 242, and 254; and
Positions 129, 177, 180, 181, 220, 224, 242, and 254.

Paragraph 44. The variant of any of paragraphs 1-31, comprising a substitution at nine positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

Paragraph 45. The variant of paragraph 44, wherein the nine positions are selected from the group consisting of:
Positions 59, 89, 129, 177, 179, 181, 220, 224, and 242;
Positions 59, 89, 129, 177, 179, 181, 220, 224, and 254;
Positions 59, 89, 129, 177, 179, 181, 220, 242, and 254;
Positions 59, 89, 129, 177, 179, 181, 224, 242, and 254;
Positions 59, 89, 129, 177, 179, 220, 224, 242, and 254;
Positions 59, 89, 129, 177, 180, 181, 220, 224, and 242;
Positions 59, 89, 129, 177, 180, 181, 220, 224, and 254;
Positions 59, 89, 129, 177, 180, 181, 220, 242, and 254;
Positions 59, 89, 129, 177, 180, 181, 224, 242, and 254;
Positions 59, 89, 129, 177, 180, 220, 224, 242, and 254;
Positions 59, 89, 129, 177, 181, 220, 224, 242, and 254;
Positions 59, 89, 129, 179, 181, 220, 224, 242, and 254;
Positions 59, 89, 129, 180, 181, 220, 224, 242, and 254;
Positions 59, 89, 177, 179, 181, 220, 224, 242, and 254;
Positions 59, 89, 177, 180, 181, 220, 224, 242, and 254;
Positions 59, 129, 177, 179, 181, 220, 224, 242, and 254;
Positions 59, 129, 177, 179, 208, 220, 224, 254, and 284;
Positions 89, 129, 177, 179, 181, 220, 224, 242, and 254; and
Positions 89, 129, 177, 180, 181, 220, 224, 242, and 254.

Paragraph 46. The variant of any of paragraphs 1-31, comprising a substitution at ten positions corresponding to any of positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427.

Paragraph 47. The variant of paragraph 46, wherein the ten positions are the positions corresponding to:
Positions 59, 89, 129, 177, 179, 181, 220, 224, 242, 254;
Positions 59, 39, 129, 177, 179, 208, 220, 224, 254, 284;
Positions 59, 89, 129, 177, 180, 181, 220, 224, 242, 254; and
Positions 59, 129, 177, 179, 208, 220, 224, 242, 254, 284.

Paragraph 48. The variant of any of paragraphs 1-47, which has 3-20, e.g., 3-10 and 6-10, alterations such as 3, 4, 5, 6, 7, 8, 9 or 10 alterations.

Paragraph 49. An isolated variant alpha-amylase, comprising or consisting of a set of substitutions selected from the group consisting of:
V59A+G108A;
S242Q+M284V;
V59A+M284V;
G108A+M284V;
V59A+G108A+M284V;
V59A+G108A+S242Q+M284V;
E129V+K177L+R179E;
K220P+N224L+Q254S;
E129V+K177L+R179E+M284V;

V59A+E129V+K177L+R179E+H208Y+M284V;
V59A+H208Y+K220P+N224L+Q254S+M284V;
E129V+K177L+R179E+K220P+N224L+Q254S;
V59A+Q89R+E129V+K177L+R179E+H208Y+K220P+
N224L+Q254S;
V59A+E129V+K177L+R179E+H208Y+K220P+
N224L+S242Q+Q254S;
V59A+Q89R+E129V+K177L+R179E+H208Y+K220P+
N224L+Q254S+M284V;
V59A+E129V+K177L+R179E+H208Y+K220P+
N224L+S242Q+Q254S+M284V;
V59A+Q89R+G108A+E129V+K177L+R179E+
H208Y+K220P+N224L+Q254S+M284V; and
V59A+G108A+E129V+K177L+R179E+H208Y+
K220P+N224L+S242Q+Q254S+M284V;
wherein the variant has at least 65% and less than 100% sequence identity with the mature polypeptide of SEQ ID NO: 1, 2, 3, 4, 5, 6, and/or 7 and the variant has alpha-amylase activity.

Paragraph 50. The variant of any of paragraphs 1-49, which has 3-20, e.g., 3-10 and 6-10, alterations such as 3, 4, 5, 6, 7, 8, 9 or 10 alterations.

Paragraph 51. The variant of paragraph 50, wherein the alterations are substitutions.

Paragraph 52. The variant of any of paragraphs 1-50, which further comprises a deletion at one or more, e.g., two, three or four, positions corresponding to positions 179, 180, 181 and 182.

Paragraph 53. The variant of paragraph 52, wherein the deletion is at positions corresponding to positions 180 and 181.

Paragraph 54. The variant of any of paragraphs 1-53, which further comprises a substitution at a position corresponding to position 193.

Paragraph 55. The variant of paragraph 54, wherein the substitution at a position corresponding to position 193 is with Phe.

Paragraph 56. The variant of any of paragraphs 1-55, which further comprises a deletion at the position corresponding to positions 376 and/or 377.

Paragraph 57. The variant of any of paragraphs 1-56, which is a variant of a parent alpha-amylase selected from the group consisting of:
   a. a polypeptide with at least 60% sequence identity with the mature polypeptide of SEQ ID NO: 1, 2, 3, 4, 5, 6, or 7; or
   b. a fragment of the mature polypeptide of SEQ ID NO: 1, 2, 3, 4, 5, 6, or 7, which has alpha-amylase activity.

Paragraph 58. The variant of paragraph 57, wherein the parent alpha-amylase has at least 60%, e.g., at least 65%, at least 70%, at least 75%, at least 80%, at least 85%, at least 90%, at least 95%, at least 96%, at least 97%, at least 98%, at least 99%, and 100% sequence identity with the mature polypeptide of SEQ ID NO: 1, 2, 3, 4, 5, 6, or 7.

Paragraph 59. The variant of paragraph 57, wherein the parent alpha-amylase comprises or consists of the amino acid sequence of the mature polypeptide of SEQ ID NO: 1, 2, 3, 4, 5, 6, or 7.

Paragraph 60. The variant of paragraph 57, wherein the parent alpha-amylase is a fragment of the amino acid sequence of the mature polypeptide of SEQ ID NO: 1, 2, 3, 4, 5, 6, or 7, wherein the fragment has alpha-amylase activity.

Paragraph 61. The variant of any of paragraphs 1-60, which is a variant of a parent wild-type alpha-amylase.

Paragraph 62. The variant of paragraph 61, wherein the parent alpha-amylase is a *Bacillus* alpha-amylase.

Paragraph 63. The variant of paragraph 62, wherein the parent alpha-amylase is a *Bacillus amyloliquefaciens, Bacillus clausii, Bacillus licheniformis, Bacillus stearothermophilus,* or *Bacillus subtilis* alpha-amylase.

Paragraph 64. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, at least 99%, but less than 100%, to the amino acid sequence of the parent alpha-amylase.

Paragraph 65. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 1.

Paragraph 66. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 2.

Paragraph 67. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 3.

Paragraph 68. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 4.

Paragraph 69. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 5.

Paragraph 70. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 6.

Paragraph 71. The variant of any of paragraphs 1-63, which has a sequence identity of at least 65%, e.g., at least 70%, at least 75%, at least 80%, at least 85%, at least 90%, at least 95%, at least 96%, at least 97%, at least 98%, and at least 99%, but less than 100%, with the mature polypeptide of SEQ ID NO: 7.

Paragraph 72. The variant of any of paragraphs 1-71, wherein the variant consists of 483 to 515, 483 to 493, or 483 to 486 amino acids.

Paragraph 73. A detergent composition comprising a variant of any of paragraphs 1-72 and a surfactant.

Paragraph 74. A composition comprising a variant of any of paragraphs 1-72 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease, and pullulanase.

Paragraph 75. Use of a variant of any of paragraphs 1-72 for washing and/or dishwashing.

Paragraph 76. Use of a variant of any of paragraphs 1-72 for desizing a textile.

Paragraph 77. Use of a variant of any of paragraphs 1-72 for producing a baked product.

Paragraph 78. Use of a variant of any of paragraphs 1-72 for liquefying a starch-containing material.

Paragraph 79. A method of producing liquefied starch, comprising liquefying a starch-containing material with a variant of any of paragraphs 1-72.

Paragraph 80. A process of producing a fermentation product, comprising
 a. liquefying a starch-containing material with a variant of any of paragraphs 1-72 to produce a liquefied mash;
 b. saccharifying the liquefied mash to produce fermentable sugars; and
 c. fermenting the fermentable sugars in the presence of a fermenting organism.

Paragraph 81. The process of paragraph 80, wherein the starch-containing material is liquefied with the variant and a pullulanase, e.g., a GH57 pullulanase.

Paragraph 82. The process of paragraph 81, wherein the pullulanase is obtained from a strain of *Thermococcus*, including *Thermococcus* sp. AM4, *Thermococcus* sp. HJ21, *Thermococcus barophilus, Thermococcus gammatolerans, Thermococcus hydrothermalis; Thermococcus kodakarensis, Thermococcus litoralis,* and *Thermococcus onnurineus*; or from a strain of *Pyrococcus*, such as *Pyrococcus abyssi* and *Pyrococcus furiosus*.

Paragraph 83. The process of any of paragraphs 80-82, further comprising adding a protease, such as an acid fungal protease or a metalloprotease before, during and/or after liquefaction.

Paragraph 84. The process of paragraph 83, wherein the metalloprotease is obtained from a strain of *Thermoascus*, preferably a strain of *Thermoascus aurantiacus*, especially *Thermoascus aurantiacus* CGMCC No. 0670.

Paragraph 85. A process of producing a fermentation product, comprising contacting a starch substrate with variant of any of paragraphs 1-72, a glucoamylase, and a fermenting organism.

Paragraph 86. The process of any of paragraphs 80-85, wherein the fermentation product is selected from the group consisting of alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

Paragraph 87. An isolated polynucleotide encoding the variant of any of paragraphs 1-72.

Paragraph 88. A nucleic acid construct comprising the polynucleotide of paragraph 87.

Paragraph 89. An expression vector comprising the nucleic acid construct of paragraph 88.

Paragraph 90. A host cell comprising the nucleic acid construct of paragraph 88.

Paragraph 91. A method of producing a variant alpha-amylase, comprising:
 a. cultivating the host cell of paragraph 90 under conditions suitable for the expression of the variant; and
 b. recovering the variant from the cultivation medium.

Paragraph 92. A transgenic plant, plant part or plant cell transformed with the polynucleotide of paragraph 87.

Paragraph 93. A method for obtaining a variant alpha-amylase, comprising
 a. introducing into a parent alpha-amylase a substitution at three or more (several) positions corresponding to positions 59, 89, 91, 96, 108, 112, 129, 157, 165, 166, 168, 171, 177, 179, 180, 181, 184, 208, 220, 224, 242, 254, 269, 270, 274, 276, 281, 284, 416, and 427, wherein the variant has at least 65% and less than 100% sequence identity with at least one of the mature polypeptide of SEQ ID NO: 1, 2, 3, 4, 5, 6, and 7, and the variant has alpha-amylase activity; and
 b. recovering the variant.

---

What is claimed is:

1. An isolated variant alpha-amylase, comprising the set of substitutions at positions E129V+K177L+R179E and at least one further amino acid substitution at a position corresponding to any of positions 59, 89, 91, 96, 108, 112, 157, 165, 166, 168, 171, 180, 181, 184, 208, 220, 224, 242, 254, 269, 270, 274, 276, 281, 284, 416, and 427, wherein the variant has at least 90% and less than 100% sequence identity with the mature polypeptide of SEQ ID NO: 1, wherein the variant has alpha-amylase activity.

2. The variant of claim 1, which comprises
   a substitution at a position corresponding to position 59 with Ala, Arg, Asn, Asp, Cys, Gln, Glu, Gly, His, Ile, Leu, Lys, Met, Phe, Pro, Ser, Thr, Trp, Tyr;
   a substitution at a position corresponding to position 89 with Ala, Arg, Asn, Asp, Cys, Glu, Gly, His, Ile, Leu, Lys, Met, Phe, Pro, Ser, Thr, Trp, Tyr, or Val;
   a substitution at a position corresponding to position 91 with Arg, Asn, Asp, Cys, Gln, Glu, Gly, His, Ile, Leu, Lys, Met, Phe, Pro, Ser, Thr, Trp, Tyr, or Val;
   a substitution at a position corresponding to position 96 with Ala, Arg, Asn, Asp, Cys, Gln, Glu, Gly, His, Ile, Leu, Lys, Phe, Pro, Ser, Thr, Trp, Tyr, or Val;
   a substitution at a position corresponding to position 108 with Ala, Arg, Asn, Asp, Cys, Gln, Glu, His, Ile, Leu, Lys, Met, Phe, Pro, Ser, Thr, Trp, Tyr, or Val;
   a substitution at a position corresponding to position 112 with Ala, Arg, Asn, Asp, Cys, Gln, Glu, His, Ile, Leu, Lys, Met, Phe, Pro, Ser, Thr, Trp, Tyr, or Val;
   a substitution at a position corresponding to position 157 with Ala, Asn, Asp, Cys, Gln, Glu, Gly, His, Ile, Leu, Lys, Met, Phe, Pro, Ser, Thr, Trp, Tyr, or Val;
   a substitution at a position corresponding to position 165 Ala, Arg, Asn, Cys, Gln, Glu, Gly, His, Ile, Leu, Lys, Met, Phe, Pro, Ser, Thr, Trp, Tyr, or Val;
   a substitution at a position corresponding to position 166 Ala, Arg, Asn, Asp, Cys, Gln, Glu, Gly, His, Ile, Leu, Lys, Met, Phe, Pro, Ser, Thr, Trp, Tyr, or Val;
   a substitution at a position corresponding to position 168 with Ala, Arg, Asn, Asp, Cys, Gln, Gly, His, Ile, Leu, Lys, Met, Phe, Pro, Ser, Thr, Trp, Tyr, or Val;
   a substitution at a position corresponding to position 171 with Ala, Arg, Asn, Asp, Cys, Gln, Glu, Gly, His, Ile, Leu, Met, Phe, Pro, Ser, Thr, Trp, Tyr, or Val;
   a substitution at a position corresponding to position 180 with Ala, Arg, Asn, Asp, Cys, Gln, Glu, Gly, His, Ile, Leu, Lys, Met, Phe, Pro, Ser, Thr, Trp, Tyr, or Val;
   a substitution at a position corresponding to position 181 with Ala, Arg, Asn, Asp, Cys, Gln, Glu, Gly, His, Leu, Lys, Met, Phe, Pro, Ser, Thr, Trp, Tyr, or Val;
   a substitution at a position corresponding to position 184 with Arg, Asn, Asp, Cys, Gln, Glu, Gly, His, Ile, Leu, Lys, Met, Phe, Pro, Ser, Thr, Trp, Tyr, or Val;
   a substitution at a position corresponding to position 208 with Ala, Arg, Asn, Asp, Cys, Gln, Glu, Gly, Ile, Leu, Lys, Met, Phe, Pro, Ser, Thr, Trp, Tyr, or Val;

a substitution at a position corresponding to position 220 with Ala, Arg, Asn, Asp, Cys, Gln, Glu, Gly, His, Ile, Leu, Met, Phe, Pro, Ser, Thr, Trp, Tyr, or Val;

a substitution at a position corresponding to position 224 with Ala, Arg, Asp, Cys, Gln, Glu, Gly, His, Ile, Leu, Lys, Met, Phe, Pro, Ser, Thr, Trp, Tyr, or Val;

a substitution at a position corresponding to position 242 with Ala, Arg, Asn, Asp, Cys, Gln, Glu, Gly, His, Ile, Leu, Lys, Met, Phe, Pro, Thr, Trp, Tyr, or Val;

a substitution at a position corresponding to position 254 with Ala, Arg, Asn, Asp, Cys, Glu, Gly, His, Ile, Leu, Lys, Met, Phe, Pro, Ser, Thr, Trp, Tyr, or Val;

a substitution at a position corresponding to position 269 with Ala, Arg, Asn, Cys, Gln, Glu, Gly, His, Ile, Leu, Lys, Met, Phe, Pro, Ser, Thr, Trp, Tyr, or Val;

a substitution at a position corresponding to position 270 with Ala, Arg, Asn, Asp, Cys, Gln, Glu, Gly, His, Leu, Lys, Met, Phe, Pro, Ser, Thr, Trp, Tyr, or Val;

a substitution at a position corresponding to position 274 with Ala, Arg, Asn, Asp, Cys, Gln, Glu, Gly, Ile, Leu, Lys, Met, Phe, Pro, Ser, Thr, Trp, Tyr, or Val;

a substitution at a position corresponding to position 276 with Ala, Arg, Asn, Asp, Cys, Gln, Glu, Gly, His, Ile, Leu, Lys, Met, Phe, Pro, Ser, Thr, Trp, or Val;

a substitution at a position corresponding to position 281 with Ala, Arg, Asn, Cys, Gln, Glu, Gly, His, Ile, Leu, Lys, Met, Phe, Pro, Ser, Thr, Trp, Tyr, or Val;

a substitution at a position corresponding to position 284 with Ala, Arg, Asn, Asp, Cys, Gln, Glu, Gly, His, Ile, Leu, Lys, Phe, Pro, Ser, Thr, Trp, Tyr, or Val;

a substitution at a position corresponding to position 416 with Ala, Arg, Asn, Asp, Cys, Gln, Glu, His, Ile, Leu, Lys, Met, Phe, Pro, Ser, Thr, Trp, Tyr, or Val; and/or a substitution at a position corresponding to position 427 with Ala, Arg, Asn, Asp, Cys, Gln, Glu, Gly, His, Ile, Lys, Met, Phe, Pro, Ser, Thr, Trp, Tyr, or Val.

3. The variant of claim 1, has at least 95% and less than 100% sequence identity, with the mature polypeptide of SEQ ID NO:1.

4. The variant of claim 1, wherein the variant has 3-20 amino acid substitutions.

5. The variant of claim 1, wherein the variant has 3, 4, 5, 6, 7, 8, 9 or 10 amino acid substitutions.

6. The variant of claim 1, which further comprises a deletion at one or more positions corresponding to positions 180, 181 and 182.

7. The variant of claim 1, which further comprises an amino acid substitution at a position corresponding to position 193.

8. The variant of claim 1, which further comprises a deletion at one or more positions corresponding to positions 376 or 377.

9. The variant of claim 1, which is a variant of a parent alpha-amylase having at least 98% sequence identity with the mature polypeptide of SEQ ID NO:1, which has alpha-amylase activity.

10. The variant of claim 9, wherein the parent alpha-amylase has at least 99% sequence identity with the mature polypeptide of SEQ ID NO:1.

11. The variant of claim 9, wherein the parent alpha-amylase is a fragment of the amino acid sequence of the mature polypeptide of SEQ ID NO:1, wherein the fragment has alpha-amylase activity.

12. The variant of claim 9, which has a sequence identity of at least 99%, but less than 100%, to the amino acid sequence of the parent alpha-amylase.

13. A detergent composition comprising a variant of claim 1 and a surfactant.

14. A method of producing liquefied starch, comprising liquefying a starch-containing material with a variant of claim 1.

15. A process of producing a fermentation product, comprising
 a. liquefying a starch-containing material with a variant of claim 1 to produce a liquefied mash;
 b. saccharifying the liquefied mash to produce fermentable sugars; and
 c. fermenting the fermentable sugars in the presence of a fermenting microorganism.

16. A process of producing a fermentation product, comprising contacting a starch substrate with variant of claim 1, a glucoamylase, and a fermenting microorganism.

* * * * *